US006787683B1

(12) United States Patent
Penna et al.

(10) Patent No.: US 6,787,683 B1
(45) Date of Patent: Sep. 7, 2004

(54) PHYTYL/PRENYLTRANSFERASE NUCLEIC ACIDS, POLYPEPTIDES AND USES THEREOF

(75) Inventors: Dean Della Penna, Williamston, MI (US); Eva Collakova, Lansing, MI (US); Sean J. Coughlan, Hockessin, DE (US); Timothy G. Helentjaris, Ankeny, IA (US)

(73) Assignees: Pioneer Hi-Bred International, Inc., Des Moines, IA (US); Board of Regents of the University and Community College Systems of Nevada on Behalf of the University of Nevada, Reno, Reno, NV (US)

( * ) Notice: Subject to any disclaimer, the term of this patent is extended or adjusted under 35 U.S.C. 154(b) by 0 days.

(21) Appl. No.: 09/560,761

(22) Filed: Apr. 28, 2000

Related U.S. Application Data

(63) Continuation-in-part of application No. 09/307,460, filed on May 7, 1999, now abandoned.

(51) Int. Cl.[7] ................................................ A01H 1/00

(52) U.S. Cl. ....................... 800/281; 800/278; 435/468

(58) Field of Search ................................ 800/278, 286, 800/298, 320.1, 312, 306, 320.3, 320, 314, 317.4, 317.1, 317.2, 315, 305; 435/468; 536/23.6, 23.2

(56) References Cited

U.S. PATENT DOCUMENTS

| 5,684,238 A | * 11/1997 | Ausich et al. ............... 800/205 |
| 6,448,475 B1 | 9/2002 | DellaPenna et al. |
| 6,541,259 B1 | 4/2003 | Lassner et al. |

FOREIGN PATENT DOCUMENTS

| WO | WO 99/04622 | 2/1999 | ............ A01H/5/00 |
| WO | WO 99/23231 | 5/1999 | ........... C12N/15/82 |
| WO | WO 00/10380 | 3/2000 | ............ A01H/5/00 |
| WO | WO 00/61771 | 10/2000 | ........... C12N/15/82 |
| WO | WO 00/63389 | 10/2000 | ........... C12N/15/53 |
| WO | WO 00/63391 | 10/2000 | ........... C12N/15/54 |
| WO | WO 01/04330 | 1/2001 | ........... C12N/15/82 |
| WO | WO 01/62781 A2 | 8/2001 | |
| WO | WO 01/79472 A2 | 10/2001 | |
| WO | WO 02/33060 | 4/2002 | ............ C12N/9/00 |
| WO | WO 02/089561 A1 | 11/2002 | |

OTHER PUBLICATIONS

Ericsson et al. Journal of Lipid Research, vol. 39, 1998, pp. 1731–1739.*
Hefner et al. Archives of Biochemistry and Biophysics. vol. 360, No. 1, Dec. 1, pp. 62–74, 1998.*
Jiang et al. Nature. vol. 366, Nov. 4, 1193, pp. 84–93.*
Elomaa et al. Molecular Breeding, vol. 2, pp. 41–50, 1996.*
Colliver et al. Plant Molecular Biology, vol. 35, pp. 509–522, 1997.*
Majeau et al. Plant Molecular Biology, vol. 25(3) pp. 377–385, 1994.*
Shintani, et al., 1998, *Science*, 282:2098–2100, "Elevating the Vitamin E Content of Plants Through Metabolic Engineering".
Tanaka, et al., 1999, *Plant Physiology*, 120: 695–704, "Reduced Activity of Geranylgeranyl Reductase Leads to Loss of Chlorphyll and Tocopherol and to Partially Geranylgeranylated Chlorophyll in Transgenic Tobacco Plants Expressing Antisene RNA for Geranylgeranyl Reductase".
Lopez, et al., 1996, "Sequence of the *bchG* Gene from *Chloroflexus aurantiacus*: Relationship between Chlorohyll Synthase and Other Polyprenyltransferases", *Journal of Bacteriology*, 178:3369–3373.
Stamm, et al., 1997, "The silence of genes in transgenic plants", *Annals of Botany*, 79: 3–12.
Koziel, et al., 1996, "Optimizing expression of transgenes with an emphasis on posttranscriptional events", *Plant Molecular Biology*, 32: 393–405.
Smith, et al., 1998, "Antisense RNA inhibition of polygalacturonase gene expression in transgenic tomatoes", *Nature*, 334: 724–726.
Yamamoto et al., 1997, GenBank Accession No. C25006, Rice cDNA from green shoot.
Nahm et al., 1998, GenBank Accession No. AA750728, Large–scale sequencing analysis of ESTs from rice immature seed.
Nahm et al., 1998, GenBank Accession No. AA749638, Large–scale sequencing analysis of ESTs from rice immature seed.
Saski et al., 1998, GenBank Accession No. AU029707, Rice cDNA from panicle.
Walbot, V., 1998, GenBank Accession No. AI612332, Maize ESTs from various cDNA libraries sequenced at Standford University.
Walbot, V., 1999, GenBank Accession No. AI711952, Maize ESTs from various cDNA libraries sequenced at Stanford University.
Walbot, V., 1999, GenBank Accession No. AI795680, Maize ESTs from various cDNA libraries sequenced at Stanford University.

(List continued on next page.)

*Primary Examiner*—Jeffrey Fredman
*Assistant Examiner*—Juliet C. Switzer
(74) *Attorney, Agent, or Firm*—Steven J. Callistein; Kathryn K. Lappegart; Pioneer Hi-Bred Intl.

(57) ABSTRACT

The invention provides isolated nucleic acids and their encoded proteins that are involved in tocopherol or plastoquinone biosynthesis. The invention further provides recombinant expression cassettes, host cells, transgenic plants, and antibody compositions. The present invention provides methods and compositions relating to altering phytyl/prenyltransferase protein content and/or composition of plants.

3 Claims, No Drawings

OTHER PUBLICATIONS

Alcala et al., 1999 GenBank Accession No. AI897027, Generation of ESTs from tomato carpel tissue.

Shoemaker et al., 1999, GenBank Accession No. AI938270, Public soybean EST project.

Shoemaker et al., 1999, GenBank Accession No. AI938569, Public soybean EST project.

Walbot, V., 1999, GenBank Accession No. AI946361, Maize ESTs from various cDNA libraries sequenced at Stanford University.

Walbot, V., 1999, GenBank Accession No. AW052841, Maize ESTs from various cDNA libraries sequenced at Stanford University.

Walbot, V., 1999, GenBank Accession No. AW054141, Maize ESTs from various cDNA libraries sequenced at Stanford Unviersity.

Walbot, V., 2000, GenBank Accession No. AW066179, Maize ESTs from various cDNA libraries sequenced at Stanford Unviersity.

Walbot, V., 1999, GenBank Accession AW146615, Maize ESTs from various cDNA libraries sequenced at Stanford University.

Shoemaker et al., 1999, GenBank Accession No. AW202246, Public soybean EST project.

Shoemaker et al., 1999, GenBank Accession No. AI444024, Public soybean EST project.

Shoemaker et al., 2000, GenBank Accession No. AI442111, Public soybean EST project.

Shoemaker et al., 1999, GenBank Accession No. AW132909, Public soybean EST project.

Shoemaker et al., 1999, GenBank Accession No. AI748688, Public soybean EST project.

Shoemaker et al., 1999, GenBank Accession No. AI939002, Public soybean EST project.

Shoemaker et al., 2000, GenBank Accession No. AW306617, Public soybean EST project.

Shoemaker et al., 2000, GenBank Accession No. AW433064, Public soybean EST project.

Saski et al., 1997, GenBank Accession No. C74444, Rice cDNA from panicle.

Cordonnier–Pratt et al., 2000, GenBank Accession No. AW563431, An EST database from Sorghum.

Lin et al., 2000, GenBank Accession No. AC003673, Sequence and analysis of chromosome 2 of the plant Arabidopsis thaliana.

Charlebois et al., 1999, GenBank Accession No. Y18930, Gene content and organization of a 281–kbp contig from the genome of the extremely thermophilic archaeon, sulfolobus solfactaricus P2.

Kaneko et al., 1999, GenBank Accession No. D90909, Sequence analysis of the genome of the unicellular cyanobacterium synechocyslis sp. strain PCC8803.II Sequence detrerminiation of the entire genome and assignment of potential protein–coding regions.

Kawarabayasi et al., 2000, GenBank Accession No. AP000058, Complete genome sequence of an aerobic hyperthermophilic crenarchaeon, aeropyrum pemix K1.

Rounsley et al., 1998, Database EBI Online AC 064625.

Walbot, V., 2000, Database EBI Online AC AW453137.

Shoemaker et al., 1999, Database EBI Online AC AW201260.

* cited by examiner

SEQUENCE LISTING

```
<160> NUMBER OF SEQ ID NOS: 32

<210> SEQ ID NO 1
<211> LENGTH: 1616
<212> TYPE: DNA
<213> ORGANISM: Arabidopsis thaliana
<220> FEATURE:
<221> NAME/KEY: CDS
<222> LOCATION: (108)...(1286)

<400> SEQUENCE: 1
gttccttcaa aatcatttct ttctcttctt tgattcccaa agatcacttc tttgtctttg      60
atttttgatt ttttttctct ctggcgtgaa ggaagaagct ttatttc atg gag tct     116
                                                    Met Glu Ser
                                                     1 ctg ctc tct agt tct tct ctt gtt tcc gct gct ggt ggg ttt tgt tgg      164
Leu Leu Ser Ser Ser Ser Leu Val Ser Ala Ala Gly Gly Phe Cys Trp
        5                  10                  15 aag aag cag aat cta aag ctc cac tct tta tca gaa atc cga gtt ctg     212
Lys Lys Gln Asn Leu Lys Leu His Ser Leu Ser Glu Ile Arg Val Leu
 20                  25                  30                  35 cgt tgt gat tcg agt aaa gtt gtc gca aaa ccg aag ttt agg aac aat     260
Arg Cys Asp Ser Ser Lys Val Val Ala Lys Pro Lys Phe Arg Asn Asn
                 40                  45                  50 ctt gtt agg cct gat ggt caa gga tct tca ttg ttg ttg tat cca aaa     308
Leu Val Arg Pro Asp Gly Gln Gly Ser Ser Leu Leu Leu Tyr Pro Lys
             55                  60                  65
```

-continued

| | | |
|---|---|---|
| cat aag tcg aga ttt cgg gtt aat gcc act gcg ggt cag cct gag gct<br>His Lys Ser Arg Phe Arg Val Asn Ala Thr Ala Gly Gln Pro Glu Ala<br>        70                          75                        80 | | 356 |
| ttc gac tcg aat agc aaa cag aag tct ttt aga gac tcg tta gat gcg<br>Phe Asp Ser Asn Ser Lys Gln Lys Ser Phe Arg Asp Ser Leu Asp Ala<br>85                        90                        95 | | 404 |
| ttt tac agg ttt tct agg cct cat aca gtt att ggc aca gtg ctt agc<br>Phe Tyr Arg Phe Ser Arg Pro His Thr Val Ile Gly Thr Val Leu Ser<br>100                      105                    110                    115 | | 452 |
| att tta tct gta tct ttc tta gca gca gag aag gtt tct gat ata tct<br>Ile Leu Ser Val Ser Phe Leu Ala Ala Glu Lys Val Ser Asp Ile Ser<br>                   120                    125                    130 | | 500 |
| cct tta ctt ttc act ggc atc ttg gag gct gtt gtt gca gct ctc atg<br>Pro Leu Leu Phe Thr Gly Ile Leu Glu Ala Val Val Ala Ala Leu Met<br>         135                    140                    145 | | 548 |
| atg aac att tac ata gtt ggg cta aat cag ttg tct gat gtt gaa ata<br>Met Asn Ile Tyr Ile Val Gly Leu Asn Gln Leu Ser Asp Val Glu Ile<br>        150                    155                    160 | | 596 |
| gat aag gtt aac aag ccc tat ctt cca ttg gca tca gga gaa tat tct<br>Asp Lys Val Asn Lys Pro Tyr Leu Pro Leu Ala Ser Gly Glu Tyr Ser<br>165                      170                    175 | | 644 |
| gtt aac acc ggc att gca ata gta gct tcc ttc tcc atc atg agt ttc<br>Val Asn Thr Gly Ile Ala Ile Val Ala Ser Phe Ser Ile Met Ser Phe<br>180                      185                    190                    195 | | 692 |
| tgg ctt ggg tgg att gtt ggt tca tgg cca ttg ttc tgg gct ctt ttt<br>Trp Leu Gly Trp Ile Val Gly Ser Trp Pro Leu Phe Trp Ala Leu Phe<br>                   200                    205                    210 | | 740 |
| gtg agt ttc atg ctc ggt act gca tac tct atc aat ttg cca ctt tta<br>Val Ser Phe Met Leu Gly Thr Ala Tyr Ser Ile Asn Leu Pro Leu Leu<br>               215                    220                    225 | | 788 |
| cgg tgg aaa aga ttt gca ttg gtt gca gca atg tgt atc ctc gct gtc<br>Arg Trp Lys Arg Phe Ala Leu Val Ala Ala Met Cys Ile Leu Ala Val<br>          230                    235                    240 | | 836 |
| cga gct att att gtt caa atc gcc ttt tat cta cat att cag aca cat<br>Arg Ala Ile Ile Val Gln Ile Ala Phe Tyr Leu His Ile Gln Thr His<br>245                      250                    255 | | 884 |
| gtg ttt gga aga cca atc ttg ttc act agg cct ctt att ttc gcc act<br>Val Phe Gly Arg Pro Ile Leu Phe Thr Arg Pro Leu Ile Phe Ala Thr<br>260                      265                    270                    275 | | 932 |
| gcg ttt atg agc ttt ttc tct gtc gtt att gca ttg ttt aag gat ata<br>Ala Phe Met Ser Phe Phe Ser Val Val Ile Ala Leu Phe Lys Asp Ile<br>                   280                    285                    290 | | 980 |
| cct gat atc gaa ggg gat aag ata ttc gga atc cga tca ttc tct gta<br>Pro Asp Ile Glu Gly Asp Lys Ile Phe Gly Ile Arg Ser Phe Ser Val<br>               295                    300                    305 | | 1028 |
| act ctg ggt cag aaa cgg gtg ttt tgg aca tgt gtt aca cta ctt caa<br>Thr Leu Gly Gln Lys Arg Val Phe Trp Thr Cys Val Thr Leu Leu Gln<br>          310                    315                    320 | | 1076 |
| atg gct tac gct gtt gca att cta gtt gga gcc aca tct cca ttc ata<br>Met Ala Tyr Ala Val Ala Ile Leu Val Gly Ala Thr Ser Pro Phe Ile<br>        325                    330                    335 | | 1124 |
| tgg agc aaa gtc atc tcg gtt gtg ggt cat gtt ata ctc gca aca act<br>Trp Ser Lys Val Ile Ser Val Val Gly His Val Ile Leu Ala Thr Thr<br>340                      345                    350                    355 | | 1172 |
| ttg tgg gct cga gct aag tcc gtt gat ctg agt agc aaa acc gaa ata<br>Leu Trp Ala Arg Ala Lys Ser Val Asp Leu Ser Ser Lys Thr Glu Ile<br>                   360                    365                    370 | | 1220 |
| act tca tgt tat atg ttc ata tgg aag ctc ttt tat gca gag tac ttg<br>Thr Ser Cys Tyr Met Phe Ile Trp Lys Leu Phe Tyr Ala Glu Tyr Leu<br>               375                    380                    385 | | 1268 |

-continued

```
ctg tta cct ttt ttg aag tgactgacat tagaagagaa gaagatggag       1316
Leu Leu Pro Phe Leu Lys
        390 ataaaagaat aagtcatcac tatgcttctg tttttattac aagttcatga aattaggtag   1376 tgaactagtg aattagagtt ttattctgaa acatggcaga ctgcaaaaat atgtcaaaga   1436 tatgaatttc tgttgggtaa agaagtctct gcttgggcaa aatcttaagg ttcggtgtgt   1496 tgatataatg ctaagcgaag aaatcgattc tatgtagaaa tttccgaaac tatgtgtaaa   1556 catgtcagaa catctccatt ctatatcttc ttctgcaaga aagctctgtt tttatcacct   1616
```

<210> SEQ ID NO 2
<211> LENGTH: 393
<212> TYPE: PRT
<213> ORGANISM: Arabidopsis thaliana

<400> SEQUENCE: 2

```
Met Glu Ser Leu Leu Ser Ser Ser Leu Val Ser Ala Ala Gly Gly
  1               5                  10                  15

Phe Cys Trp Lys Lys Gln Asn Leu Lys Leu His Ser Leu Ser Glu Ile
             20                  25                  30

Arg Val Leu Arg Cys Asp Ser Ser Lys Val Val Ala Lys Pro Lys Phe
         35                  40                  45

Arg Asn Asn Leu Val Arg Pro Asp Gly Gln Gly Ser Ser Leu Leu Leu
     50                  55                  60

Tyr Pro Lys His Lys Ser Arg Phe Arg Val Asn Ala Thr Ala Gly Gln
 65                  70                  75                  80

Pro Glu Ala Phe Asp Ser Asn Ser Lys Gln Lys Ser Phe Arg Asp Ser
                 85                  90                  95

Leu Asp Ala Phe Tyr Arg Phe Ser Arg Pro His Thr Val Ile Gly Thr
            100                 105                 110

Val Leu Ser Ile Leu Ser Val Ser Phe Leu Ala Ala Glu Lys Val Ser
        115                 120                 125

Asp Ile Ser Pro Leu Leu Phe Thr Gly Ile Leu Glu Ala Val Val Ala
    130                 135                 140

Ala Leu Met Met Asn Ile Tyr Ile Val Gly Leu Asn Gln Leu Ser Asp
145                 150                 155                 160

Val Glu Ile Asp Lys Val Asn Lys Pro Tyr Leu Pro Leu Ala Ser Gly
                165                 170                 175

Glu Tyr Ser Val Asn Thr Gly Ile Ala Ile Val Ala Ser Phe Ser Ile
            180                 185                 190

Met Ser Phe Trp Leu Gly Trp Ile Val Gly Ser Trp Pro Leu Phe Trp
        195                 200                 205

Ala Leu Phe Val Ser Phe Met Leu Gly Thr Ala Tyr Ser Ile Asn Leu
    210                 215                 220

Pro Leu Leu Arg Trp Lys Arg Phe Ala Leu Val Ala Ala Met Cys Ile
225                 230                 235                 240

Leu Ala Val Arg Ala Ile Ile Val Gln Ile Ala Phe Tyr Leu His Ile
                245                 250                 255

Gln Thr His Val Phe Gly Arg Pro Ile Leu Phe Thr Arg Pro Leu Ile
            260                 265                 270

Phe Ala Thr Ala Phe Met Ser Phe Ser Val Val Ile Ala Leu Phe
        275                 280                 285

Lys Asp Ile Pro Asp Ile Glu Gly Asp Lys Ile Phe Gly Ile Arg Ser
    290                 295                 300
```

```
Phe Ser Val Thr Leu Gly Gln Lys Arg Val Phe Trp Thr Cys Val Thr
305                 310                 315                 320

Leu Leu Gln Met Ala Tyr Ala Val Ala Ile Leu Val Gly Ala Thr Ser
            325                 330                 335

Pro Phe Ile Trp Ser Lys Val Ile Ser Val Val Gly His Val Ile Leu
        340                 345                 350

Ala Thr Thr Leu Trp Ala Arg Ala Lys Ser Val Asp Leu Ser Ser Lys
    355                 360                 365

Thr Glu Ile Thr Ser Cys Tyr Met Phe Ile Trp Lys Leu Phe Tyr Ala
370                 375                 380

Glu Tyr Leu Leu Leu Pro Phe Leu Lys
385                 390

<210> SEQ ID NO 3
<211> LENGTH: 1540
<212> TYPE: DNA
<213> ORGANISM: Zea mays
<220> FEATURE:
<221> NAME/KEY: CDS
<222> LOCATION: (21)...(1217)
<220> FEATURE:
<221> NAME/KEY: misc_feature
<222> LOCATION: (1)...(1540)
<223> OTHER INFORMATION: n = A,T,C or G

<400> SEQUENCE: 3
cgcgttcgcc cggccaaggg atg gac gcg ctt cgc cta cgg ccg tcc ctc ctc    53
                     Met Asp Ala Leu Arg Leu Arg Pro Ser Leu Leu
                       1               5                  10 ccc gtg cgg ccc ggc gcg gcc cgc ccg cga gat cat ttt cta cca cca   101
Pro Val Arg Pro Gly Ala Ala Arg Pro Arg Asp His Phe Leu Pro Pro
            15                  20                  25 tgt tgt tcc ata caa cga aat ggt gaa gga cga att tgc ttt tct agc   149
Cys Cys Ser Ile Gln Arg Asn Gly Glu Gly Arg Ile Cys Phe Ser Ser
         30                  35                  40 caa agg acc caa ggt cct acc ttg cat cac cat cag aaa ttc ttc gaa   197
Gln Arg Thr Gln Gly Pro Thr Leu His His His Gln Lys Phe Phe Glu
 45                  50                  55 tgg aaa tcc tcc tat tgt agg ata tca cat cgg tca tta aat act tct   245
Trp Lys Ser Ser Tyr Cys Arg Ile Ser His Arg Ser Leu Asn Thr Ser
 60                  65                  70                  75 gtt aat gct tcg ggg caa cag ctg cag tct gaa cct gaa aca cat gat   293
Val Asn Ala Ser Gly Gln Gln Leu Gln Ser Glu Pro Glu Thr His Asp
                 80                  85                  90 tct aca acc atc tgg agg gca ata tca tct tct cta gat gca ttt tac   341
Ser Thr Thr Ile Trp Arg Ala Ile Ser Ser Ser Leu Asp Ala Phe Tyr
             95                 100                 105 aga ttt tcc cgg cca cat act gtc ata gga aca gca tta agc ata gtc   389
Arg Phe Ser Arg Pro His Thr Val Ile Gly Thr Ala Leu Ser Ile Val
        110                 115                 120 tca gtt tcc ctt cta gct gtc cag agc ttg tct gat ata tca cct ttg   437
Ser Val Ser Leu Leu Ala Val Gln Ser Leu Ser Asp Ile Ser Pro Leu
    125                 130                 135 ttc ctc act ggt ttg ctg gag gca gtg gta gct gcc ctt ttc atg aat   485
Phe Leu Thr Gly Leu Leu Glu Ala Val Val Ala Ala Leu Phe Met Asn
140                 145                 150                 155 atc tat att gtt gga ctg aac cag tta ttc gac att gag ata gac aag   533
Ile Tyr Ile Val Gly Leu Asn Gln Leu Phe Asp Ile Glu Ile Asp Lys
                160                 165                 170 gtt aac aag cca act ctt cca ttg gca tct ggg gaa tac acc ctt gca   581
```

```
act ggg gtt gca ata gtt tcg gtc ttt gcc gct atg agc ttt ggc ctt      629
Thr Gly Val Ala Ile Val Ser Val Phe Ala Ala Met Ser Phe Gly Leu
        190                 195                 200 gga tgg gct gtt gga tca caa cct ctg ttt tgg gct ctt ttc ata agc      677
Gly Trp Ala Val Gly Ser Gln Pro Leu Phe Trp Ala Leu Phe Ile Ser
205                 210                 215 ttt gtt ctt ggg act gca tat tca atc aat ctg ccg tac ctt cga tgg      725
Phe Val Leu Gly Thr Ala Tyr Ser Ile Asn Leu Pro Tyr Leu Arg Trp
220                 225                 230                 235 aag aga ttt gct gtt gtt gca gca ctg tgc ata tta gca gtt cgt gca      773
Lys Arg Phe Ala Val Val Ala Ala Leu Cys Ile Leu Ala Val Arg Ala
                240                 245                 250 gtg att gtt cag ctg gcc ttt ttt ctc cac att cag act ttt gtt ttc      821
Val Ile Val Gln Leu Ala Phe Phe Leu His Ile Gln Thr Phe Val Phe
        255                 260                 265 agg aga ccg gca gtg ttt tct agg cca tta tta ttt gca act gga ttt      869
Arg Arg Pro Ala Val Phe Ser Arg Pro Leu Leu Phe Ala Thr Gly Phe
        270                 275                 280 atg acg ttc ttc tct gtt gta ata gca cta ttc aag gat ata cct gac      917
Met Thr Phe Phe Ser Val Val Ile Ala Leu Phe Lys Asp Ile Pro Asp
285                 290                 295 atc gaa ggg gac cgc ata ttc ggg atc cga tcc ttc agc gtc cgg tta      965
Ile Glu Gly Asp Arg Ile Phe Gly Ile Arg Ser Phe Ser Val Arg Leu
300                 305                 310                 315 ggg caa aag aag gtc ttt tgg atc tgc gtt ggc ttg ctt gag atg gcc     1013
Gly Gln Lys Lys Val Phe Trp Ile Cys Val Gly Leu Leu Glu Met Ala
                320                 325                 330 tac agc gtt gcg ata ctg atg gga gct acc tct tcc tgt ttg tgg agc     1061
Tyr Ser Val Ala Ile Leu Met Gly Ala Thr Ser Ser Cys Leu Trp Ser
        335                 340                 345 aaa aca gca acc atc gct ggc cat tcc ata ctt gcc gcg atc cta tgg     1109
Lys Thr Ala Thr Ile Ala Gly His Ser Ile Leu Ala Ala Ile Leu Trp
        350                 355                 360 agc tgc gcg cga tcg gtg gac ttg acg agc aaa gcc gca ata acg tcc     1157
Ser Cys Ala Arg Ser Val Asp Leu Thr Ser Lys Ala Ala Ile Thr Ser
365                 370                 375 ttc tac atg ttc atc tgg aag ctg ttc tac gcg gag tac ctg ctc atc     1205
Phe Tyr Met Phe Ile Trp Lys Leu Phe Tyr Ala Glu Tyr Leu Leu Ile
380                 385                 390                 395 cct ctg gtg cgg tgagcgcgag gcgaggtggt ggcagacgga tcggcgtcgg         1257
Pro Leu Val Arg cggggcggca aacaactcca cgggagaact tgagtgccgg aagtaaactc ccgtttgaaa    1317
gttgaagcgt gcaccaccgg caccgggcag agagagacac ggtggctgga tggatacgga    1377
tggccccccc aataaattcc cccgtgcatg gtaccccacg ctgcttgatg atatcccatg    1437
tgtccgggtg accggacctg atcgtctcta aanagattgg ttgcaaaaaa aaaaaaaaa    1497 aaaaaaaaa aaaaaaaaa aaaaaaaaa aaaaaaaaa aag                         1540
```

<210> SEQ ID NO 4
<211> LENGTH: 399
<212> TYPE: PRT
<213> ORGANISM: Zea mays

<400> SEQUENCE: 4

```
Met Asp Ala Leu Arg Leu Arg Pro Ser Leu Leu Pro Val Arg Pro Gly
1               5                   10                  15
```

-continued

Ala Ala Arg Pro Arg Asp His Phe Leu Pro Pro Cys Cys Ser Ile Gln
        20                  25                  30

Arg Asn Gly Glu Gly Arg Ile Cys Phe Ser Ser Gln Arg Thr Gln Gly
        35                  40                  45

Pro Thr Leu His His His Gln Lys Phe Phe Glu Trp Lys Ser Ser Tyr
        50                  55                  60

Cys Arg Ile Ser His Arg Ser Leu Asn Thr Ser Val Asn Ala Ser Gly
65                  70                  75                  80

Gln Gln Leu Gln Ser Glu Pro Glu Thr His Asp Ser Thr Thr Ile Trp
                85                  90                  95

Arg Ala Ile Ser Ser Leu Asp Ala Phe Tyr Arg Phe Ser Arg Pro
                100                 105                 110

His Thr Val Ile Gly Thr Ala Leu Ser Ile Val Ser Val Ser Leu Leu
        115                 120                 125

Ala Val Gln Ser Leu Ser Asp Ile Ser Pro Leu Phe Leu Thr Gly Leu
        130                 135                 140

Leu Glu Ala Val Val Ala Ala Leu Phe Met Asn Ile Tyr Ile Val Gly
145                 150                 155                 160

Leu Asn Gln Leu Phe Asp Ile Glu Ile Asp Lys Val Asn Lys Pro Thr
                165                 170                 175

Leu Pro Leu Ala Ser Gly Glu Tyr Thr Leu Ala Thr Gly Val Ala Ile
                180                 185                 190

Val Ser Val Phe Ala Ala Met Ser Phe Gly Leu Gly Trp Ala Val Gly
        195                 200                 205

Ser Gln Pro Leu Phe Trp Ala Leu Phe Ile Ser Phe Val Leu Gly Thr
        210                 215                 220

Ala Tyr Ser Ile Asn Leu Pro Tyr Leu Arg Trp Lys Arg Phe Ala Val
225                 230                 235                 240

Val Ala Ala Leu Cys Ile Leu Ala Val Arg Ala Val Ile Val Gln Leu
                245                 250                 255

Ala Phe Phe Leu His Ile Gln Thr Phe Val Phe Arg Arg Pro Ala Val
                260                 265                 270

Phe Ser Arg Pro Leu Leu Phe Ala Thr Gly Phe Met Thr Phe Phe Ser
        275                 280                 285

Val Val Ile Ala Leu Phe Lys Asp Ile Pro Asp Ile Glu Gly Asp Arg
        290                 295                 300

Ile Phe Gly Ile Arg Ser Phe Ser Val Arg Leu Gly Gln Lys Lys Val
305                 310                 315                 320

Phe Trp Ile Cys Val Gly Leu Leu Glu Met Ala Tyr Ser Val Ala Ile
                325                 330                 335

Leu Met Gly Ala Thr Ser Ser Cys Leu Trp Ser Lys Thr Ala Thr Ile
                340                 345                 350

Ala Gly His Ser Ile Leu Ala Ala Ile Leu Trp Ser Cys Ala Arg Ser
        355                 360                 365

Val Asp Leu Thr Ser Lys Ala Ala Ile Thr Ser Phe Tyr Met Phe Ile
        370                 375                 380

Trp Lys Leu Phe Tyr Ala Glu Tyr Leu Leu Ile Pro Leu Val Arg
385                 390                 395

<210> SEQ ID NO 5
<211> LENGTH: 28
<212> TYPE: DNA
<213> ORGANISM: Artificial Sequence
<220> FEATURE:
<223> OTHER INFORMATION: Arabidopsis thaliana

```
<400> SEQUENCE: 5
ttgttttcag gctgttgttg cagctctc                                          28

<210> SEQ ID NO 6
<211> LENGTH: 28
<212> TYPE: DNA
<213> ORGANISM: Artificial Sequence
<220> FEATURE:
<223> OTHER INFORMATION: Arabidopsis thaliana

<400> SEQUENCE: 6
cgtttctgac ccagagttac agagaatg                                          28

<210> SEQ ID NO 7
<211> LENGTH: 30
<212> TYPE: DNA
<213> ORGANISM: Artificial Sequence
<220> FEATURE:
<223> OTHER INFORMATION: Synechocystis

<400> SEQUENCE: 7
tattcatatg gcaactatcc aagcttttg                                         30

<210> SEQ ID NO 8
<211> LENGTH: 32
<212> TYPE: DNA
<213> ORGANISM: Artificial Sequence
<220> FEATURE:
<223> OTHER INFORMATION: Synechocystis

<400> SEQUENCE: 8
ggatcctaat tgaagaagat actaaatagt tc                                     32

<210> SEQ ID NO 9
<211> LENGTH: 927
<212> TYPE: DNA
<213> ORGANISM: Synechocystis
<220> FEATURE:
<221> NAME/KEY: CDS
<222> LOCATION: (1)...(927)
<223> OTHER INFORMATION:

<400> SEQUENCE: 9 atg gca act atc caa gct ttt tgg cgc ttc tcc cgc ccc cat acc atc        48
Met Ala Thr Ile Gln Ala Phe Trp Arg Phe Ser Arg Pro His Thr Ile
 1               5                  10                  15 att ggt aca act ctg agc gtc tgg gct gtg tat ctg tta act att ctc        96
Ile Gly Thr Thr Leu Ser Val Trp Ala Val Tyr Leu Leu Thr Ile Leu
             20                  25                  30 ggg gat gga aac tca gtt aac tcc cct gct tcc ctg gat tta gtg ttc       144
Gly Asp Gly Asn Ser Val Asn Ser Pro Ala Ser Leu Asp Leu Val Phe
         35                  40                  45 ggc gct tgg ctg gcc tgc ctg ttg ggt aat gtg tac att gtc ggc ctc       192
Gly Ala Trp Leu Ala Cys Leu Leu Gly Asn Val Tyr Ile Val Gly Leu
     50                  55                  60 aac caa ttg tgg gat gtg gac att gac cgc atc aat aag ccg aat ttg       240
Asn Gln Leu Trp Asp Val Asp Ile Asp Arg Ile Asn Lys Pro Asn Leu
 65                  70                  75                  80 ccc cta gct aac gga gat ttt tct atc gcc cag ggc cgt tgg att gtg       288
Pro Leu Ala Asn Gly Asp Phe Ser Ile Ala Gln Gly Arg Trp Ile Val
                 85                  90                  95 gga ctt tgt ggc gtt gct tcc ttg gcg atc gcc tgg gga tta ggg cta       336
Gly Leu Cys Gly Val Ala Ser Leu Ala Ile Ala Trp Gly Leu Gly Leu
```

```
tgg ctg ggg cta acg gtg ggc att agt ttg att att ggc acg gcc tat    384
Trp Leu Gly Leu Thr Val Gly Ile Ser Leu Ile Ile Gly Thr Ala Tyr
            115                 120                 125 tcg gtg ccg cca gtg agg tta aag cgc ttt tcc ctg ctg gcg gcc ctg    432
Ser Val Pro Pro Val Arg Leu Lys Arg Phe Ser Leu Leu Ala Ala Leu
        130                 135                 140 tgt att ctg acg gtg cgg gga att gtg gtt aac ttg ggc tta ttt tta    480
Cys Ile Leu Thr Val Arg Gly Ile Val Val Asn Leu Gly Leu Phe Leu
145                 150                 155                 160 ttt ttt aga att ggt tta ggt tat ccc ccc act tta ata acc ccc atc    528
Phe Phe Arg Ile Gly Leu Gly Tyr Pro Pro Thr Leu Ile Thr Pro Ile
                165                 170                 175 tgg gtt ttg act tta ttt atc tta gtt ttc acc gtg gcg atc gcc att    576
Trp Val Leu Thr Leu Phe Ile Leu Val Phe Thr Val Ala Ile Ala Ile
            180                 185                 190 ttt aaa gat gtg cca gat atg gaa ggc gat cgg caa ttt aag att caa    624
Phe Lys Asp Val Pro Asp Met Glu Gly Asp Arg Gln Phe Lys Ile Gln
        195                 200                 205 act tta act ttg caa atc ggc aaa caa aac gtt ttt cgg gga acc tta    672
Thr Leu Thr Leu Gln Ile Gly Lys Gln Asn Val Phe Arg Gly Thr Leu
    210                 215                 220 att tta ctc act ggt tgt tat tta gcc atg gca atc tgg ggc tta tgg    720
Ile Leu Leu Thr Gly Cys Tyr Leu Ala Met Ala Ile Trp Gly Leu Trp
225                 230                 235                 240 gcg gct atg cct tta aat act gct ttc ttg att gtt tcc cat ttg tgc    768
Ala Ala Met Pro Leu Asn Thr Ala Phe Leu Ile Val Ser His Leu Cys
                245                 250                 255 tta tta gcc tta ctc tgg tgg cgg agt cga gat gta cac tta gaa agc    816
Leu Leu Ala Leu Leu Trp Trp Arg Ser Arg Asp Val His Leu Glu Ser
            260                 265                 270 aaa acc gaa att gct agt ttt tat cag ttt att tgg aag cta ttt ttc    864
Lys Thr Glu Ile Ala Ser Phe Tyr Gln Phe Ile Trp Lys Leu Phe Phe
        275                 280                 285 tta gag tac ttg ctg tat ccc ttg gct ctg tgg tta cct aat ttt tct    912
Leu Glu Tyr Leu Leu Tyr Pro Leu Ala Leu Trp Leu Pro Asn Phe Ser
    290                 295                 300 aat act att ttt tag                                                927
Asn Thr Ile Phe *
305

<210> SEQ ID NO 10
<211> LENGTH: 308
<212> TYPE: PRT
<213> ORGANISM: Synechocystis

<400> SEQUENCE: 10

Met Ala Thr Ile Gln Ala Phe Trp Arg Phe Ser Arg Pro His Thr Ile
1               5                   10                  15

Ile Gly Thr Thr Leu Ser Val Trp Ala Val Tyr Leu Leu Thr Ile Leu
                20                  25                  30

Gly Asp Gly Asn Ser Val Asn Ser Pro Ala Ser Leu Asp Leu Val Phe
            35                  40                  45

Gly Ala Trp Leu Ala Cys Leu Leu Gly Asn Val Tyr Ile Val Gly Leu
        50                  55                  60

Asn Gln Leu Trp Asp Val Asp Ile Asp Arg Ile Asn Lys Pro Asn Leu
65                  70                  75                  80

Pro Leu Ala Asn Gly Asp Phe Ser Ile Ala Gln Gly Arg Trp Ile Val
                85                  90                  95
```

```
Gly Leu Cys Gly Val Ala Ser Leu Ala Ile Ala Trp Gly Leu Gly Leu
                100                 105                 110
Trp Leu Gly Leu Thr Val Gly Ile Ser Leu Ile Ile Gly Thr Ala Tyr
            115                 120                 125
Ser Val Pro Pro Val Arg Leu Lys Arg Phe Ser Leu Leu Ala Ala Leu
        130                 135                 140
Cys Ile Leu Thr Val Arg Gly Ile Val Val Asn Leu Gly Leu Phe Leu
145                 150                 155                 160
Phe Phe Arg Ile Gly Leu Gly Tyr Pro Pro Thr Leu Ile Thr Pro Ile
                165                 170                 175
Trp Val Leu Thr Leu Phe Ile Leu Val Phe Thr Val Ala Ile Ala Ile
            180                 185                 190
Phe Lys Asp Val Pro Asp Met Glu Gly Asp Arg Gln Phe Lys Ile Gln
        195                 200                 205
Thr Leu Thr Leu Gln Ile Gly Lys Gln Asn Val Phe Arg Gly Thr Leu
    210                 215                 220
Ile Leu Leu Thr Gly Cys Tyr Leu Ala Met Ala Ile Trp Gly Leu Trp
225                 230                 235                 240
Ala Ala Met Pro Leu Asn Thr Ala Phe Leu Ile Val Ser His Leu Cys
                245                 250                 255
Leu Leu Ala Leu Leu Trp Trp Arg Ser Arg Asp Val His Leu Glu Ser
            260                 265                 270
Lys Thr Glu Ile Ala Ser Phe Tyr Gln Phe Ile Trp Lys Leu Phe Phe
        275                 280                 285
Leu Glu Tyr Leu Leu Tyr Pro Leu Ala Leu Trp Leu Pro Asn Phe Ser
    290                 295                 300
Asn Thr Ile Phe
305

<210> SEQ ID NO 11
<211> LENGTH: 1278
<212> TYPE: DNA
<213> ORGANISM: Zea mays
<220> FEATURE:
<221> NAME/KEY: CDS
<222> LOCATION: (106)...(879)

<400> SEQUENCE: 11
tcgcaaagac gctgcatgcc ttctatcagt tctgccgacc acacacaata tttggaacca      60
taataggcat tacttcggtg tctatcctgc cagtgaaaga gcctg gac gat ttt acg    117
                                                Asp Asp Phe Thr
                                                 1 ttg ata gct ata tgg gga ttt ctc gag gct ttg gcc gcc gca tta tgt      165
Leu Ile Ala Ile Trp Gly Phe Leu Glu Ala Leu Ala Ala Ala Leu Cys
  5                  10                  15                  20 atg aac gtt tat gta gta ggg ctg aac aag gtc aat aag cca acc ctc      213
Met Asn Val Tyr Val Val Gly Leu Asn Lys Val Asn Lys Pro Thr Leu
                 25                  30                  35 cca tta tcg ttc gga gag ttt tca atg cca act gca gta ttg tta gta      261
Pro Leu Ser Phe Gly Glu Phe Ser Met Pro Thr Ala Val Leu Leu Val
             40                  45                  50 gtg gca ttc ttg gtc atg agc att agc atc gga ata aga tca aag tct      309
Val Ala Phe Leu Val Met Ser Ile Ser Ile Gly Ile Arg Ser Lys Ser
         55                  60                  65 gct cca ttg atg tgt gct ttg ctt gtt tgc ttc ctt ctt gga agc gca      357
Ala Pro Leu Met Cys Ala Leu Leu Val Cys Phe Leu Leu Gly Ser Ala
     70                  75                  80
```

```
tac ccc att gac gtc cca tta ctc cgg tgg aag cga cat gct ttt cta      405
Tyr Pro Ile Asp Val Pro Leu Leu Arg Trp Lys Arg His Ala Phe Leu
 85                  90                  95                 100 gct gca ttc tgc ata atc ttt gtg agg cct gta gtg gtc cag tta gct      453
Ala Ala Phe Cys Ile Ile Phe Val Arg Pro Val Val Val Gln Leu Ala
                105                 110                 115 ttc ttt gca cac atg cag caa cat gtt ctg aag agg ccc ttg gca cct      501
Phe Phe Ala His Met Gln Gln His Val Leu Lys Arg Pro Leu Ala Pro
            120                 125                 130 aca agg tcg gtg gtc ttt gca aca tgt ttc atg tgt tgc ttc gct gca      549
Thr Arg Ser Val Val Phe Ala Thr Cys Phe Met Cys Cys Phe Ala Ala
        135                 140                 145 gta ata gcg cta ttc aag gat att cct gat gtc gat gga gat aga gat      597
Val Ile Ala Leu Phe Lys Asp Ile Pro Asp Val Asp Gly Asp Arg Asp
150                 155                 160 ttc ggc att cag tcc atg act gta cga tta ggc caa cag aga gtg cat      645
Phe Gly Ile Gln Ser Met Thr Val Arg Leu Gly Gln Gln Arg Val His
165                 170                 175                 180 agg ctc tgc att aat att ctc atg aca gca tac gca gcc gca att ttg      693
Arg Leu Cys Ile Asn Ile Leu Met Thr Ala Tyr Ala Ala Ala Ile Leu
                185                 190                 195 gta ggc gcg tca tct acg aac ctg tat cag aag att gtc att gtg tct      741
Val Gly Ala Ser Ser Thr Asn Leu Tyr Gln Lys Ile Val Ile Val Ser
            200                 205                 210 ggt cat ggc ttg ctt gcc tcc aca ctc tgg caa aga gca caa caa ttt      789
Gly His Gly Leu Leu Ala Ser Thr Leu Trp Gln Arg Ala Gln Gln Phe
        215                 220                 225 gac att gag aat aag gat tgt atc aca caa ttt tat atg ttc att tgg      837
Asp Ile Glu Asn Lys Asp Cys Ile Thr Gln Phe Tyr Met Phe Ile Trp
230                 235                 240 aag tta ttc tac gcc gag tat ttt ctt ata cca ttt gtg tag              879
Lys Leu Phe Tyr Ala Glu Tyr Phe Leu Ile Pro Phe Val  *
245                 250                 255 taaagaatca tgcgaagaac aacaccctg ctatagacat gtgaaggttt attgctaatg    939
ttactctacc ccctgctata gacatgtgaa ggtttattgc taatgttact ctaccgaatg    999
gtctgaatgt ctatgcgtca tttgaatgta atatgactat tgttgtatc agggtaacaa   1059 ctggagcaaa tgtaccatgt atattaagca ttaatttaac tgcatcattt gtaccatgta   1119
tattatgact atgtatgaga tattgtctct tattagtact ggatgtgatg tgtcttatta   1179
tgactatgga tgagactttt gtgatgtaat tgatgagact atggttttaa atattgttat   1239
gtgattgtgt gtgagataaa aaaaaaaaa aaaaaaaa                            1278

<210> SEQ ID NO 12
<211> LENGTH: 257
<212> TYPE: PRT
<213> ORGANISM: Zea mays

<400> SEQUENCE: 12

Asp Asp Phe Thr Leu Ile Ala Ile Trp Gly Phe Leu Glu Ala Leu Ala
 1               5                  10                  15

Ala Ala Leu Cys Met Asn Val Tyr Val Gly Leu Asn Lys Val Asn
                20                  25                  30

Lys Pro Thr Leu Pro Leu Ser Phe Gly Glu Phe Ser Met Pro Thr Ala
            35                  40                  45

Val Leu Leu Val Val Ala Phe Leu Val Met Ser Ile Ser Ile Gly Ile
        50                  55                  60
```

```
Arg Ser Lys Ser Ala Pro Leu Met Cys Ala Leu Leu Val Cys Phe Leu
 65                  70                  75                  80

Leu Gly Ser Ala Tyr Pro Ile Asp Val Pro Leu Leu Arg Trp Lys Arg
                 85                  90                  95

His Ala Phe Leu Ala Ala Phe Cys Ile Ile Phe Val Arg Pro Val Val
            100                 105                 110

Val Gln Leu Ala Phe Phe Ala His Met Gln Gln His Val Leu Lys Arg
        115                 120                 125

Pro Leu Ala Pro Thr Arg Ser Val Val Phe Ala Thr Cys Phe Met Cys
    130                 135                 140

Cys Phe Ala Ala Val Ile Ala Leu Phe Lys Asp Ile Pro Asp Val Asp
145                 150                 155                 160

Gly Asp Arg Asp Phe Gly Ile Gln Ser Met Thr Val Arg Leu Gly Gln
                165                 170                 175

Gln Arg Val His Arg Leu Cys Ile Asn Ile Leu Met Thr Ala Tyr Ala
            180                 185                 190

Ala Ala Ile Leu Val Gly Ala Ser Ser Thr Asn Leu Tyr Gln Lys Ile
        195                 200                 205

Val Ile Val Ser Gly His Gly Leu Leu Ala Ser Thr Leu Trp Gln Arg
    210                 215                 220

Ala Gln Gln Phe Asp Ile Glu Asn Lys Asp Cys Ile Thr Gln Phe Tyr
225                 230                 235                 240

Met Phe Ile Trp Lys Leu Phe Tyr Ala Glu Tyr Phe Leu Ile Pro Phe
                245                 250                 255

Val

<210> SEQ ID NO 13
<211> LENGTH: 1771
<212> TYPE: DNA
<213> ORGANISM: Zea mays
<220> FEATURE:
<221> NAME/KEY: CDS
<222> LOCATION: (1)...(1149)

<400> SEQUENCE: 13 cca cgc gtc cgg gcc tcc ctt cct ctc ccg ccc agt act gcc gtc acc    48
Pro Arg Val Arg Ala Ser Leu Pro Leu Pro Pro Ser Thr Ala Val Thr
  1               5                  10                  15 gct cgc ttc ctc gcc gcc ccc gcc atc cgc gtg atc agc cca tcg agg    96
Ala Arg Phe Leu Ala Ala Pro Ala Ile Arg Val Ile Ser Pro Ser Arg
             20                  25                  30 ccc gcg ctg ccg ctc ctc tca tcc gcc tcc gca ggc ggc ttc cct cac   144
Pro Ala Leu Pro Leu Leu Ser Ser Ala Ser Ala Gly Gly Phe Pro His
         35                  40                  45 gcc tct cgc gct ccc tgc agt gcc gcc cgc gag cac cgc cgc ggc acc   192
Ala Ser Arg Ala Pro Cys Ser Ala Ala Arg Glu His Arg Arg Gly Thr
     50                  55                  60 gtg cgg gaa tgc tct cga gct gat gct gct gga gca gct cca tta tca   240
Val Arg Glu Cys Ser Arg Ala Asp Ala Ala Gly Ala Ala Pro Leu Ser
 65                  70                  75                  80 aag aca ctg tta gac ctc aag gat tcc tgc tgg aga ttt tta agg cca   288
Lys Thr Leu Leu Asp Leu Lys Asp Ser Cys Trp Arg Phe Leu Arg Pro
                 85                  90                  95 cat aca atc cga gga act gct tta gga tcc ata gca ttg gtt gcg aga   336
His Thr Ile Arg Gly Thr Ala Leu Gly Ser Ile Ala Leu Val Ala Arg
            100                 105                 110 gcc ttg ata gag aat tcc cat ctg ata aac tgg tgg ttg ata ttc aaa   384
Ala Leu Ile Glu Asn Ser His Leu Ile Asn Trp Trp Leu Ile Phe Lys
        115                 120                 125
```

-continued

|  |  |  |  |  |  |  |  |  |  |  |  |  |  |  |  |
|---|---|---|---|---|---|---|---|---|---|---|---|---|---|---|---|
|  |  | 115 |  |  |  | 120 |  |  |  | 125 |  |  |  |  |  |
| gca | ttc | tat | gga | ctt | ggg | gca | ttg | ata | ttt | ggc | aat | ggt | tac | ata | gtt | 432 |
| Ala | Phe | Tyr | Gly | Leu | Gly | Ala | Leu | Ile | Phe | Gly | Asn | Gly | Tyr | Ile | Val |  |
|  | 130 |  |  |  | 135 |  |  |  | 140 |  |  |  |  |  |  |
| ggg | att | aat | cag | atc | tat | gat | gtt | gct | att | gac | aag | gta | aac | aag | cca | 480 |
| Gly | Ile | Asn | Gln | Ile | Tyr | Asp | Val | Ala | Ile | Asp | Lys | Val | Asn | Lys | Pro |  |
| 145 |  |  |  |  | 150 |  |  |  |  | 155 |  |  |  |  | 160 |  |
| tat | tta | ccc | att | gct | gct | ggt | gat | ctc | tca | att | cag | tca | gca | tgg | ttg | 528 |
| Tyr | Leu | Pro | Ile | Ala | Ala | Gly | Asp | Leu | Ser | Ile | Gln | Ser | Ala | Trp | Leu |  |
|  |  |  |  | 165 |  |  |  |  | 170 |  |  |  |  | 175 |  |  |
| ttg | gtg | ata | tta | ttt | gca | gct | gca | ggt | ttt | tca | att | gtt | ata | tca | aac | 576 |
| Leu | Val | Ile | Leu | Phe | Ala | Ala | Ala | Gly | Phe | Ser | Ile | Val | Ile | Ser | Asn |  |
|  |  |  | 180 |  |  |  |  | 185 |  |  |  |  | 190 |  |  |  |
| ttt | gga | cct | ttc | att | acc | tct | cta | tac | tgc | ctt | ggc | cta | ttt | ctt | ggc | 624 |
| Phe | Gly | Pro | Phe | Ile | Thr | Ser | Leu | Tyr | Cys | Leu | Gly | Leu | Phe | Leu | Gly |  |
|  |  | 195 |  |  |  |  | 200 |  |  |  |  | 205 |  |  |  |  |
| act | ata | tat | tct | gtt | cct | cca | ttt | aga | ctg | aag | aga | tat | ccg | gtt | gct | 672 |
| Thr | Ile | Tyr | Ser | Val | Pro | Pro | Phe | Arg | Leu | Lys | Arg | Tyr | Pro | Val | Ala |  |
|  | 210 |  |  |  |  | 215 |  |  |  |  | 220 |  |  |  |  |  |
| gct | ttt | ctt | atc | att | gca | acg | gtt | cgt | ggt | ttc | ctt | ctc | aac | ttt | ggc | 720 |
| Ala | Phe | Leu | Ile | Ile | Ala | Thr | Val | Arg | Gly | Phe | Leu | Leu | Asn | Phe | Gly |  |
| 225 |  |  |  |  | 230 |  |  |  |  | 235 |  |  |  |  | 240 |  |
| gtg | tac | tat | gct | act | agg | gct | gca | cta | ggt | ctt | aca | ttc | caa | tgg | agc | 768 |
| Val | Tyr | Tyr | Ala | Thr | Arg | Ala | Ala | Leu | Gly | Leu | Thr | Phe | Gln | Trp | Ser |  |
|  |  |  |  | 245 |  |  |  |  | 250 |  |  |  |  | 255 |  |  |
| tcc | cct | gtt | gct | ttc | att | aca | tgc | ttc | gtg | aca | cta | ttt | gct | ttg | gtc | 816 |
| Ser | Pro | Val | Ala | Phe | Ile | Thr | Cys | Phe | Val | Thr | Leu | Phe | Ala | Leu | Val |  |
|  |  |  | 260 |  |  |  |  | 265 |  |  |  |  | 270 |  |  |  |
| att | gct | ata | acc | aaa | gat | ctc | cct | gat | gtt | gaa | gga | gat | cgc | aag | tat | 864 |
| Ile | Ala | Ile | Thr | Lys | Asp | Leu | Pro | Asp | Val | Glu | Gly | Asp | Arg | Lys | Tyr |  |
|  |  | 275 |  |  |  |  | 280 |  |  |  |  | 285 |  |  |  |  |
| caa | ata | tca | act | ttg | gca | aca | aag | ctt | ggt | gtc | aga | aat | att | gca | ttc | 912 |
| Gln | Ile | Ser | Thr | Leu | Ala | Thr | Lys | Leu | Gly | Val | Arg | Asn | Ile | Ala | Phe |  |
|  | 290 |  |  |  |  | 295 |  |  |  |  | 300 |  |  |  |  |  |
| ctt | gga | tct | ggt | tta | tta | tta | gca | aac | tat | att | gct | gct | att | gct | gta | 960 |
| Leu | Gly | Ser | Gly | Leu | Leu | Leu | Ala | Asn | Tyr | Ile | Ala | Ala | Ile | Ala | Val |  |
| 305 |  |  |  |  | 310 |  |  |  |  | 315 |  |  |  |  | 320 |  |
| gct | ttt | acc | atg | cct | cag | gat | ttc | agg | tgc | act | gta | atg | gtt | cct | gtg | 1008 |
| Ala | Phe | Thr | Met | Pro | Gln | Asp | Phe | Arg | Cys | Thr | Val | Met | Val | Pro | Val |  |
|  |  |  |  | 325 |  |  |  |  | 330 |  |  |  |  | 335 |  |  |
| cat | gct | gtc | ctt | gct | ggt | ggt | tta | att | ttc | cag | aca | tgg | gtt | ctg | gag | 1056 |
| His | Ala | Val | Leu | Ala | Gly | Gly | Leu | Ile | Phe | Gln | Thr | Trp | Val | Leu | Glu |  |
|  |  |  | 340 |  |  |  |  | 345 |  |  |  |  | 350 |  |  |  |
| caa | gcg | aag | tac | aga | aag | gat | gct | att | tcg | cag | tac | tat | cgg | ttc | ata | 1104 |
| Gln | Ala | Lys | Tyr | Arg | Lys | Asp | Ala | Ile | Ser | Gln | Tyr | Tyr | Arg | Phe | Ile |  |
|  |  | 355 |  |  |  |  | 360 |  |  |  |  | 365 |  |  |  |  |
| tgg | aat | ctc | ttc | tat | gct | gaa | tat | atc | ttc | ttc | ccg | tta | ata | tag |  | 1149 |
| Trp | Asn | Leu | Phe | Tyr | Ala | Glu | Tyr | Ile | Phe | Phe | Pro | Leu | Ile | * |  |  |
|  | 370 |  |  |  |  | 375 |  |  |  |  | 380 |  |  |  |  |  |

| | |
|---|---|
| agagatcttg tagttcatct tgatcttggg ctacagccta attcatggga gcaaatgaaa | 1209 |
| agagggagaa gttggcaaag tgaggtctgt tgtgcatatt tcaacggaa acaatggagt | 1269 |
| agcaatattg ctatgctagg gttctgaagt tgtaggagct tttcgaagct tttacgatgt | 1329 |
| tgaaggcgtt gttgttggag ctgtggaagc tgtttttctt tttttccttt tgtatcaaca | 1389 |
| gtgtcgcgtt ctgtacggtc ttacttggaa gtgctttgac ctttgaacac atgggttgaa | 1449 |
| gcttgagatc tggtcccgaa cagatggcgg tggaacggcc aagacaagct tgtttcatgc | 1509 |
| cactcgaggt cgaggctaaa ccactacggc gtgctcttcc atgaaacgca gaaaactagg | 1569 |

-continued

```
gaaatgacta tatatatggt gcaatacgtt gtatattttc tgagtttcag ctcgtatata    1629
tagtaggaac ctcaacttttt accccatcga ttggaagact gaaacttctt gcatgcgtat    1689
```
```
gaaatgacta tatatatggt gcaatacgtt gtatattttc tgagtttcag ctcgtatata    1629
tagtaggaac ctcaactttt accccatcga ttggaagact gaaacttctt gcatgcgtat    1689
gtatgcctgt gggtatgtaa aaaccttggc ccgcacaaag ctacatgtta cagaactttc    1749
agctcaaaaa aaaaaaaaaa ag                                             1771
```

<210> SEQ ID NO 14
<211> LENGTH: 382
<212> TYPE: PRT
<213> ORGANISM: Zea mays

<400> SEQUENCE: 14

```
Pro Arg Val Arg Ala Ser Leu Pro Leu Pro Pro Ser Thr Ala Val Thr
 1               5                  10                  15

Ala Arg Phe Leu Ala Ala Pro Ala Ile Arg Val Ile Ser Pro Ser Arg
            20                  25                  30

Pro Ala Leu Pro Leu Leu Ser Ser Ala Ser Ala Gly Gly Phe Pro His
        35                  40                  45

Ala Ser Arg Ala Pro Cys Ser Ala Ala Arg Glu His Arg Arg Gly Thr
    50                  55                  60

Val Arg Glu Cys Ser Arg Ala Asp Ala Ala Gly Ala Ala Pro Leu Ser
65                  70                  75                  80

Lys Thr Leu Leu Asp Leu Lys Asp Ser Cys Trp Arg Phe Leu Arg Pro
                85                  90                  95

His Thr Ile Arg Gly Thr Ala Leu Gly Ser Ile Ala Leu Val Ala Arg
            100                 105                 110

Ala Leu Ile Glu Asn Ser His Leu Ile Asn Trp Trp Leu Ile Phe Lys
        115                 120                 125

Ala Phe Tyr Gly Leu Gly Ala Leu Ile Phe Gly Asn Gly Tyr Ile Val
    130                 135                 140

Gly Ile Asn Gln Ile Tyr Asp Val Ala Ile Asp Lys Val Asn Lys Pro
145                 150                 155                 160

Tyr Leu Pro Ile Ala Ala Gly Asp Leu Ser Ile Gln Ser Ala Trp Leu
                165                 170                 175

Leu Val Ile Leu Phe Ala Ala Gly Phe Ser Ile Val Ile Ser Asn
            180                 185                 190

Phe Gly Pro Phe Ile Thr Ser Leu Tyr Cys Leu Gly Leu Phe Leu Gly
        195                 200                 205

Thr Ile Tyr Ser Val Pro Pro Phe Arg Leu Lys Arg Tyr Pro Val Ala
    210                 215                 220

Ala Phe Leu Ile Ile Ala Thr Val Arg Gly Phe Leu Leu Asn Phe Gly
225                 230                 235                 240

Val Tyr Tyr Ala Thr Arg Ala Ala Leu Gly Leu Thr Phe Gln Trp Ser
                245                 250                 255

Ser Pro Val Ala Phe Ile Thr Cys Phe Val Thr Leu Phe Ala Leu Val
            260                 265                 270

Ile Ala Ile Thr Lys Asp Leu Pro Asp Val Glu Gly Asp Arg Lys Tyr
        275                 280                 285

Gln Ile Ser Thr Leu Ala Thr Lys Leu Gly Val Arg Asn Ile Ala Phe
    290                 295                 300

Leu Gly Ser Gly Leu Leu Leu Ala Asn Tyr Ile Ala Ala Ile Ala Val
305                 310                 315                 320

Ala Phe Thr Met Pro Gln Asp Phe Arg Cys Thr Val Met Val Pro Val
                325                 330                 335
```

```
His Ala Val Leu Ala Gly Gly Leu Ile Phe Gln Thr Trp Val Leu Glu
        340                 345                 350

Gln Ala Lys Tyr Arg Lys Asp Ala Ile Ser Gln Tyr Tyr Arg Phe Ile
        355                 360                 365

Trp Asn Leu Phe Tyr Ala Glu Tyr Ile Phe Phe Pro Leu Ile
        370                 375                 380

<210> SEQ ID NO 15
<211> LENGTH: 1618
<212> TYPE: DNA
<213> ORGANISM: Oryza sativa
<220> FEATURE:
<221> NAME/KEY: CDS
<222> LOCATION: (59)...(1273)

<400> SEQUENCE: 15
gcacgagctt acaagccgcc gcgcgcgccc ggccgccgcg gtggtggcgg cggcggcg        58 atg gat tcg ctg cgc ctc cgg ccg tcg ctc ctc gcc gcg cgg gcc ccc       106
Met Asp Ser Leu Arg Leu Arg Pro Ser Leu Leu Ala Ala Arg Ala Pro
  1               5                  10                  15 ggc gcg gcc tcg ctg ccg cct ctc cgg cga gat cac ttt cta cca cct       154
Gly Ala Ala Ser Leu Pro Pro Leu Arg Arg Asp His Phe Leu Pro Pro
                 20                  25                  30 tta tgt tct atc cat aga aat ggt aaa cgg cca gtt tct ttg tcc agc       202
Leu Cys Ser Ile His Arg Asn Gly Lys Arg Pro Val Ser Leu Ser Ser
         35                  40                  45 caa agg acc caa ggt cct tcc ttc gat caa tgt cag aaa ttc ttt ggt       250
Gln Arg Thr Gln Gly Pro Ser Phe Asp Gln Cys Gln Lys Phe Phe Gly
 50                  55                  60 tgg aaa tcc tcc cac cac agg ata cca cat cga cca aca tct agt tcc       298
Trp Lys Ser Ser His His Arg Ile Pro His Arg Pro Thr Ser Ser Ser
 65                  70                  75                  80 gct gac gct tcg gga caa cct cta caa tct tca gct gaa gca cat gat       346
Ala Asp Ala Ser Gly Gln Pro Leu Gln Ser Ser Ala Glu Ala His Asp
                 85                  90                  95 tca tca agt ata tgg aag cca ata tca tct tct ccg gat gca ttt tac       394
Ser Ser Ser Ile Trp Lys Pro Ile Ser Ser Ser Pro Asp Ala Phe Tyr
            100                 105                 110 agg ttt tct cgg cca cat act gtc ata gga aca gca ctt agc ata gtc       442
Arg Phe Ser Arg Pro His Thr Val Ile Gly Thr Ala Leu Ser Ile Val
        115                 120                 125 tca gtt tcg ctg cta gct gtt gag aat ttg tcc gat gtg tct ccc ttg       490
Ser Val Ser Leu Leu Ala Val Glu Asn Leu Ser Asp Val Ser Pro Leu
    130                 135                 140 ttc ctc act ggt ttg ctg gag gca gtg gta gca gct ctt ttc atg aac       538
Phe Leu Thr Gly Leu Leu Glu Ala Val Val Ala Ala Leu Phe Met Asn
145                 150                 155                 160 atc tat atc gtt gga ttg aat cag ttg ttc gac att gag ata gat aag       586
Ile Tyr Ile Val Gly Leu Asn Gln Leu Phe Asp Ile Glu Ile Asp Lys
                165                 170                 175 gtt aac aag cca act ctt cca tta gca tct ggg gaa tat tct cct gca       634
Val Asn Lys Pro Thr Leu Pro Leu Ala Ser Gly Glu Tyr Ser Pro Ala
            180                 185                 190 act gga gtt gca ctt gta tca gcc ttc gct gct atg agc ttt ggc ctt       682
Thr Gly Val Ala Leu Val Ser Ala Phe Ala Ala Met Ser Phe Gly Leu
        195                 200                 205 gga tgg gct gtt gga tca cag cct ctg ttc ctg gct ctt ttc att agc       730
Gly Trp Ala Val Gly Ser Gln Pro Leu Phe Leu Ala Leu Phe Ile Ser
    210                 215                 220
```

```
ttt att ctt gga aca gca tat tcg att aat ctg cca ttc ctg aga tgg      778
Phe Ile Leu Gly Thr Ala Tyr Ser Ile Asn Leu Pro Phe Leu Arg Trp
225                 230                 235                 240 aag aga tct gct gtt gtt gca gca ctt tgc ata tta gca gtc cgt gca      826
Lys Arg Ser Ala Val Val Ala Ala Leu Cys Ile Leu Ala Val Arg Ala
                245                 250                 255 gtg att gtt cag ctg gca ttt ttt ctc cac att cag aca ttc gta ttc      874
Val Ile Val Gln Leu Ala Phe Phe Leu His Ile Gln Thr Phe Val Phe
            260                 265                 270 aga aga cca gca gtc ttt acc agg cca ttg att ttt gca act gca ttc      922
Arg Arg Pro Ala Val Phe Thr Arg Pro Leu Ile Phe Ala Thr Ala Phe
        275                 280                 285 atg acc ttt ttc tcc gtt gta ata gca ttg ttc aag gat ata cct gat      970
Met Thr Phe Phe Ser Val Val Ile Ala Leu Phe Lys Asp Ile Pro Asp
    290                 295                 300 att gaa gga gac cgt att ttt ggt atc aaa tct ttc agt gtt cga tta     1018
Ile Glu Gly Asp Arg Ile Phe Gly Ile Lys Ser Phe Ser Val Arg Leu
305                 310                 315                 320 ggt caa aag aag gtt ttc tgg att tgt gtt ggt ctg ctc gag atg gct     1066
Gly Gln Lys Lys Val Phe Trp Ile Cys Val Gly Leu Leu Glu Met Ala
                325                 330                 335 tat tgt gtt gca ata ttg atg gga gct act tct gcc tgt ttg tgg agc     1114
Tyr Cys Val Ala Ile Leu Met Gly Ala Thr Ser Ala Cys Leu Trp Ser
            340                 345                 350 aaa tac gca act gtg gtg gga cat gca atc ctt gcg gca atc cta tgg     1162
Lys Tyr Ala Thr Val Val Gly His Ala Ile Leu Ala Ala Ile Leu Trp
        355                 360                 365 aac cgc tca cgg tcg att gat ctg aca agc aaa act gca atc act tct     1210
Asn Arg Ser Arg Ser Ile Asp Leu Thr Ser Lys Thr Ala Ile Thr Ser
    370                 375                 380 ttc tac atg ttt atc tgg aag ctg ttc tac gcg gaa tac ctt ctc att     1258
Phe Tyr Met Phe Ile Trp Lys Leu Phe Tyr Ala Glu Tyr Leu Leu Ile
385                 390                 395                 400 cct ctt gta agg tga caaaggcgat tactccaggt agattggaat tggatcatgg     1313
Pro Leu Val Arg * ctggatggat gaacggacgg cgccccataa aatcacctgc aaatcacccg gtacacatgt   1373
tgacatcctg catccagata tgatattgat agatcatcgt cggcaccatc attcctctga   1433
aagatttcgc acggcatttc aacctccaac tcccaacgta ccccaaaaaa agtaactagg   1493
ccaggtgagc atctgctagc ctatagtaga cgttattgga acagtggtag tacttgttag   1553
cagcagtaat aataatcatc ataataaagc tctgggttac tgtcaaaaaa aaaaaaaaa    1613 aaaaa                                                               1618

<210> SEQ ID NO 16
<211> LENGTH: 404
<212> TYPE: PRT
<213> ORGANISM: Oryza sativa

<400> SEQUENCE: 16

Met Asp Ser Leu Arg Leu Arg Pro Ser Leu Leu Ala Ala Arg Ala Pro
1               5                   10                  15

Gly Ala Ala Ser Leu Pro Pro Leu Arg Arg Asp His Phe Leu Pro Pro
            20                  25                  30

Leu Cys Ser Ile His Arg Asn Gly Lys Arg Pro Val Ser Leu Ser Ser
        35                  40                  45

Gln Arg Thr Gln Gly Pro Ser Phe Asp Gln Cys Gln Lys Phe Phe Gly
    50                  55                  60
```

-continued

```
Trp Lys Ser Ser His His Arg Ile Pro His Arg Pro Thr Ser Ser Ser
 65                  70                  75                  80

Ala Asp Ala Ser Gly Gln Pro Leu Gln Ser Ala Glu Ala His Asp
                 85                  90                  95

Ser Ser Ser Ile Trp Lys Pro Ile Ser Ser Ser Pro Asp Ala Phe Tyr
                100                 105                 110

Arg Phe Ser Arg Pro His Thr Val Ile Gly Thr Ala Leu Ser Ile Val
                115                 120                 125

Ser Val Ser Leu Leu Ala Val Glu Asn Leu Ser Asp Val Ser Pro Leu
            130                 135                 140

Phe Leu Thr Gly Leu Leu Glu Ala Val Val Ala Ala Leu Phe Met Asn
145                 150                 155                 160

Ile Tyr Ile Val Gly Leu Asn Gln Leu Phe Asp Ile Glu Ile Asp Lys
                165                 170                 175

Val Asn Lys Pro Thr Leu Pro Leu Ala Ser Gly Glu Tyr Ser Pro Ala
            180                 185                 190

Thr Gly Val Ala Leu Val Ser Ala Phe Ala Ala Met Ser Phe Gly Leu
            195                 200                 205

Gly Trp Ala Val Gly Ser Gln Pro Leu Phe Leu Ala Leu Phe Ile Ser
210                 215                 220

Phe Ile Leu Gly Thr Ala Tyr Ser Ile Asn Leu Pro Phe Leu Arg Trp
225                 230                 235                 240

Lys Arg Ser Ala Val Val Ala Ala Leu Cys Ile Leu Ala Val Arg Ala
                245                 250                 255

Val Ile Val Gln Leu Ala Phe Phe Leu His Ile Gln Thr Phe Val Phe
                260                 265                 270

Arg Arg Pro Ala Val Phe Thr Arg Pro Leu Ile Phe Ala Thr Ala Phe
            275                 280                 285

Met Thr Phe Phe Ser Val Val Ile Ala Leu Phe Lys Asp Ile Pro Asp
290                 295                 300

Ile Glu Gly Asp Arg Ile Phe Gly Ile Lys Ser Phe Ser Val Arg Leu
305                 310                 315                 320

Gly Gln Lys Lys Val Phe Trp Ile Cys Val Gly Leu Leu Glu Met Ala
                325                 330                 335

Tyr Cys Val Ala Ile Leu Met Gly Ala Thr Ser Ala Cys Leu Trp Ser
                340                 345                 350

Lys Tyr Ala Thr Val Val Gly His Ala Ile Leu Ala Ala Ile Leu Trp
            355                 360                 365

Asn Arg Ser Arg Ser Ile Asp Leu Thr Ser Lys Thr Ala Ile Thr Ser
370                 375                 380

Phe Tyr Met Phe Ile Trp Lys Leu Phe Tyr Ala Glu Tyr Leu Leu Ile
385                 390                 395                 400

Pro Leu Val Arg
```

<210> SEQ ID NO 17
<211> LENGTH: 1733
<212> TYPE: DNA
<213> ORGANISM: Oryza Sativa
<220> FEATURE:
<221> NAME/KEY: CDS
<222> LOCATION: (1)...(1137)

<400> SEQUENCE: 17

```
ctt aca ctc gcc tcc cct cct ctc ccc tgc cgc gcc gcc gcc acc gcc     48
Leu Thr Leu Ala Ser Pro Pro Leu Pro Cys Arg Ala Ala Ala Thr Ala
  1               5                  10                  15
```

-continued

| | |
|---|---|
| agc cgc agc ggg cgt cct gct ccg cgc ctc ctc ggc cct ccg ccg ccg<br>Ser Arg Ser Gly Arg Pro Ala Pro Arg Leu Leu Gly Pro Pro Pro Pro<br>               20                      25                 30 | 96 |
| ccc gct tcc cct ctc ctc tcc tcc gct tcg gcg cgc ttc ccg cgt gcc<br>Pro Ala Ser Pro Leu Leu Ser Ser Ala Ser Ala Arg Phe Pro Arg Ala<br>          35                    40                    45 | 144 |
| ccc tgc aac gcc gca cgc tgg agc cgg cgc gac gcc gtg cgg gtt tgc<br>Pro Cys Asn Ala Ala Arg Trp Ser Arg Arg Asp Ala Val Arg Val Cys<br>50                      55                    60 | 192 |
| tct caa gct ggt gca gct gga cca gcc cca tta tcg aag aca ttg tca<br>Ser Gln Ala Gly Ala Ala Gly Pro Ala Pro Leu Ser Lys Thr Leu Ser<br>65                      70                    75                 80 | 240 |
| gac ctc aag gat tcc tgc tgg aga ttt tta cgg cca cat aca att cga<br>Asp Leu Lys Asp Ser Cys Trp Arg Phe Leu Arg Pro His Thr Ile Arg<br>                   85                      90                 95 | 288 |
| gga act gcc ttg gga tcc ata gca tta gtt gct aga gct ttg ata gag<br>Gly Thr Ala Leu Gly Ser Ile Ala Leu Val Ala Arg Ala Leu Ile Glu<br>          100                    105               110 | 336 |
| aac ccc caa ctg ata aat tgg tgg ttg gta ttc aaa gcg ttc tat ggg<br>Asn Pro Gln Leu Ile Asn Trp Trp Leu Val Phe Lys Ala Phe Tyr Gly<br>          115                    120               125 | 384 |
| ctc gtg gcg tta atc tgt ggc aat ggt tac atc gtt ggg atc aat cag<br>Leu Val Ala Leu Ile Cys Gly Asn Gly Tyr Ile Val Gly Ile Asn Gln<br>130                    135                  140 | 432 |
| atc tat gac att aga atc gat aag gta aac aag cca tat tta cca att<br>Ile Tyr Asp Ile Arg Ile Asp Lys Val Asn Lys Pro Tyr Leu Pro Ile<br>145                    150                  155               160 | 480 |
| gct gcc ggt gat ctc tca gtt cag aca gca tgg tta ttg gtg gta tta<br>Ala Ala Gly Asp Leu Ser Val Gln Thr Ala Trp Leu Leu Val Val Leu<br>                  165                  170               175 | 528 |
| ttt gca gct gcg gga ttt tca att gtt gtg aca aac ttt gga cct ttc<br>Phe Ala Ala Ala Gly Phe Ser Ile Val Val Thr Asn Phe Gly Pro Phe<br>                180                  185               190 | 576 |
| att acc tct cta tat tgc ctt ggt cta ttt ctt ggc acc ata tac tct<br>Ile Thr Ser Leu Tyr Cys Leu Gly Leu Phe Leu Gly Thr Ile Tyr Ser<br>          195                    200               205 | 624 |
| gtt cct cca ttc aga ctt aag aga tat cct gtt gct gct ttt ctt atc<br>Val Pro Pro Phe Arg Leu Lys Arg Tyr Pro Val Ala Ala Phe Leu Ile<br>210                    215                  220 | 672 |
| att gca acg gtc cgt ggt ttt ctt ctc aac ttt ggt gtg tac tat gct<br>Ile Ala Thr Val Arg Gly Phe Leu Leu Asn Phe Gly Val Tyr Tyr Ala<br>225                    230                  235               240 | 720 |
| act aga gca gca ctg ggt ctt aca ttc caa tgg agc tcg cct gtt gct<br>Thr Arg Ala Ala Leu Gly Leu Thr Phe Gln Trp Ser Ser Pro Val Ala<br>                245                  250               255 | 768 |
| ttc att aca tgc ttc gtg act tta ttt gct ttg gtc att gct ata acc<br>Phe Ile Thr Cys Phe Val Thr Leu Phe Ala Leu Val Ile Ala Ile Thr<br>          260                    265               270 | 816 |
| aaa gat ctc cca gat gtt gaa ggg gat cgg aag tat caa ata tca act<br>Lys Asp Leu Pro Asp Val Glu Gly Asp Arg Lys Tyr Gln Ile Ser Thr<br>275                    280                  285 | 864 |
| ttg gcg aca aag ctc ggt gtc aga aac att gca ttt ctt ggc tct ggt<br>Leu Ala Thr Lys Leu Gly Val Arg Asn Ile Ala Phe Leu Gly Ser Gly<br>          290                    295               300 | 912 |
| tta ttg ata gca aat tat gtt gct gct att gct gta gct ttt ctc atg<br>Leu Leu Ile Ala Asn Tyr Val Ala Ala Ile Ala Val Ala Phe Leu Met<br>305                    310                  315               320 | 960 |
| cct cag gct ttc agg cgc act gta atg gtg cct gtg cat gct gcc ctt<br>Pro Gln Ala Phe Arg Arg Thr Val Met Val Pro Val His Ala Ala Leu | 1008 |

-continued

```
                    325                 330                 335
gcc gtt ggt ata att ttc cag aca tgg gtt ctg gag caa gca aaa tat     1056
Ala Val Gly Ile Ile Phe Gln Thr Trp Val Leu Glu Gln Ala Lys Tyr
                340                 345                 350 act aag gat gct att tca cag tac tac cgg ttc att tgg aat ctc ttc     1104
Thr Lys Asp Ala Ile Ser Gln Tyr Tyr Arg Phe Ile Trp Asn Leu Phe
        355                 360                 365 tat gct gaa tac atc ttc ttc ccg ttg ata tag agaccaagca atctgatatg   1157
Tyr Ala Glu Tyr Ile Phe Phe Pro Leu Ile  *
    370                 375 gtctgcatgt tgagtgcggc aaaaactaga agcccatatg aacagtggga gtaagggaac   1217
gaacatgcca tccatgggaa gactctgata actctctctc gcccgggctg taaagggtaa   1277
gcactgttgt gcatatatat gaaggaagg tgataaagca gggatgctaa attgctactg    1337
ggatccttaa aggcttatag tggtcaccag tggaatgtgc cttaataatt tggttaccta   1397
gcagagcaag ttttttgcagg ttattaggta atatctttga gggaatgaac ttagatttca  1457
ttgttttaag gtctggtcac acaacgggta gtagttctgg agcggcaaaa gacgaccttg   1517
ttttacacta ccaagggagg ttaactctag ttttcatgtg accacttacc ttgagagttg   1577
agaccatgga atcacttgtc gactcctcgg cttgtatatt tctagtgtca gcatttgcat   1637
tctcctccac acttgtactt gaagagttga agacaacttt tttgtttgtg tatttctgga   1697
gtgtcagcat ttgcattcaa aaaaaaaaaa aaaaaa                             1733
```

<210> SEQ ID NO 18
<211> LENGTH: 378
<212> TYPE: PRT
<213> ORGANISM: Oryza Sativa

<400> SEQUENCE: 18

```
Leu Thr Leu Ala Ser Pro Pro Leu Pro Cys Arg Ala Ala Thr Ala
 1               5                  10                  15

Ser Arg Ser Gly Arg Pro Ala Pro Arg Leu Leu Gly Pro Pro Pro
            20                  25                  30

Pro Ala Ser Pro Leu Leu Ser Ser Ala Ser Ala Arg Phe Pro Arg Ala
        35                  40                  45

Pro Cys Asn Ala Ala Arg Trp Ser Arg Arg Asp Ala Val Arg Val Cys
    50                  55                  60

Ser Gln Ala Gly Ala Ala Gly Pro Ala Pro Leu Ser Lys Thr Leu Ser
65                  70                  75                  80

Asp Leu Lys Asp Ser Cys Trp Arg Phe Leu Arg Pro His Thr Ile Arg
                85                  90                  95

Gly Thr Ala Leu Gly Ser Ile Ala Leu Val Ala Arg Ala Leu Ile Glu
            100                 105                 110

Asn Pro Gln Leu Ile Asn Trp Trp Leu Val Phe Lys Ala Phe Tyr Gly
        115                 120                 125

Leu Val Ala Leu Ile Cys Gly Asn Gly Tyr Ile Val Gly Ile Asn Gln
    130                 135                 140

Ile Tyr Asp Ile Arg Ile Asp Lys Val Asn Lys Pro Tyr Leu Pro Ile
145                 150                 155                 160

Ala Ala Gly Asp Leu Ser Val Gln Thr Ala Trp Leu Leu Val Val Leu
                165                 170                 175

Phe Ala Ala Ala Gly Phe Ser Ile Val Val Thr Asn Phe Gly Pro Phe
            180                 185                 190

Ile Thr Ser Leu Tyr Cys Leu Gly Leu Phe Leu Gly Thr Ile Tyr Ser
```

```
                195                 200                 205
Val Pro Pro Phe Arg Leu Lys Arg Tyr Pro Val Ala Ala Phe Leu Ile
    210                 215                 220

Ile Ala Thr Val Arg Gly Phe Leu Leu Asn Phe Gly Val Tyr Tyr Ala
225                 230                 235                 240

Thr Arg Ala Ala Leu Gly Leu Thr Phe Gln Trp Ser Ser Pro Val Ala
                245                 250                 255

Phe Ile Thr Cys Phe Val Thr Leu Phe Ala Leu Val Ile Ala Ile Thr
                260                 265                 270

Lys Asp Leu Pro Asp Val Glu Gly Asp Arg Lys Tyr Gln Ile Ser Thr
    275                 280                 285

Leu Ala Thr Lys Leu Gly Val Arg Asn Ile Ala Phe Leu Gly Ser Gly
    290                 295                 300

Leu Leu Ile Ala Asn Tyr Val Ala Ala Ile Ala Val Ala Phe Leu Met
305                 310                 315                 320

Pro Gln Ala Phe Arg Arg Thr Val Met Val Pro Val His Ala Ala Leu
                325                 330                 335

Ala Val Gly Ile Ile Phe Gln Thr Trp Val Leu Glu Gln Ala Lys Tyr
                340                 345                 350

Thr Lys Asp Ala Ile Ser Gln Tyr Tyr Arg Phe Ile Trp Asn Leu Phe
    355                 360                 365

Tyr Ala Glu Tyr Ile Phe Phe Pro Leu Ile
    370                 375

<210> SEQ ID NO 19
<211> LENGTH: 1400
<212> TYPE: DNA
<213> ORGANISM: Glycine max
<220> FEATURE:
<221> NAME/KEY: CDS
<222> LOCATION: (37)...(1203)

<400> SEQUENCE: 19
ctgcagggtt ttttcgtttg ctgtgttcag ctccctt atg gag ctc tca ctc tct       54
                                        Met Glu Leu Ser Leu Ser
                                          1               5 cca act tca cat cgt gtt cct tcc aca att ccc act ttg aat ttc gct      102
Pro Thr Ser His Arg Val Pro Ser Thr Ile Pro Thr Leu Asn Phe Ala
             10                  15                  20 aaa cta tca ttc act aag gcc aca acg tcc caa cct ttg ttc tta gga      150
Lys Leu Ser Phe Thr Lys Ala Thr Thr Ser Gln Pro Leu Phe Leu Gly
         25                  30                  35 ttt tcc aaa cac ttc aac tca att ggg ttg aac cat cac agt tac aga      198
Phe Ser Lys His Phe Asn Ser Ile Gly Leu Asn His His Ser Tyr Arg
     40                  45                  50 tgc tgc tca aat gct gtt cct aag aga ccc caa aga ccc agt tcc ata      246
Cys Cys Ser Asn Ala Val Pro Lys Arg Pro Gln Arg Pro Ser Ser Ile
 55                  60                  65                  70 agg gcc tgc act gga gtt gga gct gct ggt tct gat cgt cca tta gct      294
Arg Ala Cys Thr Gly Val Gly Ala Ala Gly Ser Asp Arg Pro Leu Ala
                 75                  80                  85 gaa aga ctt tta gat ttg aaa gat gct tgc tgg aga ttt tta agg cca      342
Glu Arg Leu Leu Asp Leu Lys Asp Ala Cys Trp Arg Phe Leu Arg Pro
             90                  95                 100 cat act ata cgt ggt aca gca cta ggt tca ttt gct ttg gtg gca aga      390
His Thr Ile Arg Gly Thr Ala Leu Gly Ser Phe Ala Leu Val Ala Arg
        105                 110                 115 gca ttg att gag aac acg aat ttg ata aag tgg tct ctt ttg ttc aaa      438
```

```
Ala Leu Ile Glu Asn Thr Asn Leu Ile Lys Trp Ser Leu Leu Phe Lys
        120                 125                 130 gct ttc tct ggt ctt ttt gcc ctg att tgt ggg aat ggt tat ata gtt    486
Ala Phe Ser Gly Leu Phe Ala Leu Ile Cys Gly Asn Gly Tyr Ile Val
135                 140                 145                 150 ggc atc aat caa atc tat gac att agc att gac aag gta aac aaa cct    534
Gly Ile Asn Gln Ile Tyr Asp Ile Ser Ile Asp Lys Val Asn Lys Pro
            155                 160                 165 tat tta cct ata gct gct gga gat ctt tct gtc caa tct gca tgg ttc    582
Tyr Leu Pro Ile Ala Ala Gly Asp Leu Ser Val Gln Ser Ala Trp Phe
        170                 175                 180 ttg gtt ata ttt ttt gca gca gct ggc ctg tcg att gca ggg ttg aac    630
Leu Val Ile Phe Phe Ala Ala Ala Gly Leu Ser Ile Ala Gly Leu Asn
    185                 190                 195 ttt ggg cct ttc att ttt tct ctt tac aca ctt ggc ctt ttc ttg gga    678
Phe Gly Pro Phe Ile Phe Ser Leu Tyr Thr Leu Gly Leu Phe Leu Gly
200                 205                 210 acc atc tat tct gtt cct cca ttg agg atg aaa cgc ttt cct gtt gca    726
Thr Ile Tyr Ser Val Pro Pro Leu Arg Met Lys Arg Phe Pro Val Ala
215                 220                 225                 230 gca ttt ctt ata att gcc acg gta cgt ggt ttt ctc ctt aac ttt ggt    774
Ala Phe Leu Ile Ile Ala Thr Val Arg Gly Phe Leu Leu Asn Phe Gly
                235                 240                 245 gtg tac tat gcc act aga gct tcc ctt ggg ctt gca ttt gaa tgg agc    822
Val Tyr Tyr Ala Thr Arg Ala Ser Leu Gly Leu Ala Phe Glu Trp Ser
            250                 255                 260 tct cct gtg gtt ttt atc aca aca ttt gta aca ttt ttc gca ctg gta    870
Ser Pro Val Val Phe Ile Thr Thr Phe Val Thr Phe Phe Ala Leu Val
        265                 270                 275 att gct ata aca aaa gat ctt cct gat gtt gaa ggt gat cgc aag tat    918
Ile Ala Ile Thr Lys Asp Leu Pro Asp Val Glu Gly Asp Arg Lys Tyr
    280                 285                 290 cag ata tca acc ttt gct aca aaa tta gga gtt cgg aac att gct ttc    966
Gln Ile Ser Thr Phe Ala Thr Lys Leu Gly Val Arg Asn Ile Ala Phe
295                 300                 305                 310 ctt ggt tct gga att ttg ctg gtg aat tat att gtt tct gtt ttg gca   1014
Leu Gly Ser Gly Ile Leu Leu Val Asn Tyr Ile Val Ser Val Leu Ala
                315                 320                 325 gca att tat atg cct cag gct ttc agg cgt tgg tta ctc ata cca gct   1062
Ala Ile Tyr Met Pro Gln Ala Phe Arg Arg Trp Leu Leu Ile Pro Ala
            330                 335                 340 cat aca att ttt gca ata agc ttg att tac cag gca cga ata tta gaa   1110
His Thr Ile Phe Ala Ile Ser Leu Ile Tyr Gln Ala Arg Ile Leu Glu
        345                 350                 355 caa gca aat tat acc aag gat gca ata tca gga ttc tat cga ttc ata   1158
Gln Ala Asn Tyr Thr Lys Asp Ala Ile Ser Gly Phe Tyr Arg Phe Ile
    360                 365                 370 tgg aat ctg ttc tat gct gag tat gca ata ttt cct ttc ata tag       1203
Trp Asn Leu Phe Tyr Ala Glu Tyr Ala Ile Phe Pro Phe Ile *
375                 380                 385 caaaccttgc tactttttc ttgggaaaag gtgcatacgt gcatagttag agagatcttt   1263
gtttatcaag tgtcaattgg taaactagct atcattattt ttttaaaatg agtattgttg   1323
tatataaatg tgatactatt tccttttact ttgacgtaat gccattaaca tatttcataa   1383
aaaaaaaaaa aaaaaa                                                  1400

<210> SEQ ID NO 20
<211> LENGTH: 388
<212> TYPE: PRT
```

-continued

<213> ORGANISM: Glycine max

<400> SEQUENCE: 20

```
Met Glu Leu Ser Leu Ser Pro Thr Ser His Arg Val Pro Ser Thr Ile
1               5                   10                  15

Pro Thr Leu Asn Phe Ala Lys Leu Ser Phe Thr Lys Ala Thr Thr Ser
            20                  25                  30

Gln Pro Leu Phe Leu Gly Phe Ser Lys His Phe Asn Ser Ile Gly Leu
        35                  40                  45

Asn His His Ser Tyr Arg Cys Cys Ser Asn Ala Val Pro Lys Arg Pro
    50                  55                  60

Gln Arg Pro Ser Ser Ile Arg Ala Cys Thr Gly Val Gly Ala Ala Gly
65                  70                  75                  80

Ser Asp Arg Pro Leu Ala Glu Arg Leu Leu Asp Leu Lys Asp Ala Cys
                85                  90                  95

Trp Arg Phe Leu Arg Pro His Thr Ile Arg Gly Thr Ala Leu Gly Ser
            100                 105                 110

Phe Ala Leu Val Ala Arg Ala Leu Ile Glu Asn Thr Asn Leu Ile Lys
        115                 120                 125

Trp Ser Leu Leu Phe Lys Ala Phe Ser Gly Leu Phe Ala Leu Ile Cys
    130                 135                 140

Gly Asn Gly Tyr Ile Val Gly Ile Asn Gln Ile Tyr Asp Ile Ser Ile
145                 150                 155                 160

Asp Lys Val Asn Lys Pro Tyr Leu Pro Ile Ala Ala Gly Asp Leu Ser
                165                 170                 175

Val Gln Ser Ala Trp Phe Leu Val Ile Phe Ala Ala Ala Gly Leu
            180                 185                 190

Ser Ile Ala Gly Leu Asn Phe Gly Pro Phe Ile Phe Ser Leu Tyr Thr
        195                 200                 205

Leu Gly Leu Phe Leu Gly Thr Ile Tyr Ser Val Pro Pro Leu Arg Met
    210                 215                 220

Lys Arg Phe Pro Val Ala Ala Phe Leu Ile Ile Ala Thr Val Arg Gly
225                 230                 235                 240

Phe Leu Leu Asn Phe Gly Val Tyr Tyr Ala Thr Arg Ala Ser Leu Gly
                245                 250                 255

Leu Ala Phe Glu Trp Ser Ser Pro Val Val Phe Ile Thr Thr Phe Val
            260                 265                 270

Thr Phe Phe Ala Leu Val Ile Ala Ile Thr Lys Asp Leu Pro Asp Val
        275                 280                 285

Glu Gly Asp Arg Lys Tyr Gln Ile Ser Thr Phe Ala Thr Lys Leu Gly
    290                 295                 300

Val Arg Asn Ile Ala Phe Leu Gly Ser Gly Ile Leu Leu Val Asn Tyr
305                 310                 315                 320

Ile Val Ser Val Leu Ala Ala Ile Tyr Met Pro Gln Ala Phe Arg Arg
                325                 330                 335

Trp Leu Leu Ile Pro Ala His Thr Ile Phe Ala Ile Ser Leu Ile Tyr
            340                 345                 350

Gln Ala Arg Ile Leu Glu Gln Ala Asn Tyr Thr Lys Asp Ala Ile Ser
        355                 360                 365

Gly Phe Tyr Arg Phe Ile Trp Asn Leu Phe Tyr Ala Glu Tyr Ala Ile
    370                 375                 380

Phe Pro Phe Ile
385
```

-continued

```
<210> SEQ ID NO 21
<211> LENGTH: 1370
<212> TYPE: DNA
<213> ORGANISM: Glycine max
<220> FEATURE:
<221> NAME/KEY: CDS
<222> LOCATION: (24)...(1211)

<400> SEQUENCE: 21
gcacgagagc actactgtta tat atg gat tcg atg ctt ctt cga tct ttt cct       53
                         Met Asp Ser Met Leu Leu Arg Ser Phe Pro
                          1               5                  10 aat att aac aac gct tct tct ctc gcc acc act ggt tct tat ttg cca        101
Asn Ile Asn Asn Ala Ser Ser Leu Ala Thr Thr Gly Ser Tyr Leu Pro
                 15                  20                  25 aat gct tca tgg cac aat agg aaa atc caa aaa gaa tat aat ttt ttg        149
Asn Ala Ser Trp His Asn Arg Lys Ile Gln Lys Glu Tyr Asn Phe Leu
             30                  35                  40 agg ttt cgg tgg cca agt ttg aac cac cat tac aaa agc att gaa gga        197
Arg Phe Arg Trp Pro Ser Leu Asn His His Tyr Lys Ser Ile Glu Gly
         45                  50                  55 ggg tgt aca tgt aaa aaa tgt aat ata aaa ttt gtt gtg aaa gcg acc        245
Gly Cys Thr Cys Lys Lys Cys Asn Ile Lys Phe Val Val Lys Ala Thr
 60                  65                  70 tct gaa aaa tct ttt gag tct gaa cct caa gct ttt gat cca aaa agc        293
Ser Glu Lys Ser Phe Glu Ser Glu Pro Gln Ala Phe Asp Pro Lys Ser
 75                  80                  85                  90 att ttg gac tct gtc aag aat tcc ttg gat gct ttc tac agg ttt tcc        341
Ile Leu Asp Ser Val Lys Asn Ser Leu Asp Ala Phe Tyr Arg Phe Ser
                 95                 100                 105 aga cct cac aca gtt att ggc aca gca tta agc ata att tct gtg tcc        389
Arg Pro His Thr Val Ile Gly Thr Ala Leu Ser Ile Ile Ser Val Ser
            110                 115                 120 ctc ctt gct gtt gag aaa ata tca gat ata tct cca tta ttt ttt act        437
Leu Leu Ala Val Glu Lys Ile Ser Asp Ile Ser Pro Leu Phe Phe Thr
        125                 130                 135 ggt gtg ttg gag gct gtg gtt gct gcc ctg ttt atg aat att tat att        485
Gly Val Leu Glu Ala Val Val Ala Ala Leu Phe Met Asn Ile Tyr Ile
    140                 145                 150 gtt ggt ttg aat caa ttg tct gat gtt gaa ata gac aag ata aac aag        533
Val Gly Leu Asn Gln Leu Ser Asp Val Glu Ile Asp Lys Ile Asn Lys
155                 160                 165                 170 ccg tat ctt cca tta gca tct ggg gaa tat tcc ttt gaa act ggt gtc        581
Pro Tyr Leu Pro Leu Ala Ser Gly Glu Tyr Ser Phe Glu Thr Gly Val
                175                 180                 185 act att gtt gca tct ttt tca att ctg agt ttt tgg ctt ggc tgg gtt        629
Thr Ile Val Ala Ser Phe Ser Ile Leu Ser Phe Trp Leu Gly Trp Val
            190                 195                 200 gta ggt tca tgg cca tta ttt tgg gcc ctt ttt gta agc ttt gtg cta        677
Val Gly Ser Trp Pro Leu Phe Trp Ala Leu Phe Val Ser Phe Val Leu
        205                 210                 215 gga act gct tat tca atc aat gtg cct ctg ttg aga tgg aag agg ttt        725
Gly Thr Ala Tyr Ser Ile Asn Val Pro Leu Leu Arg Trp Lys Arg Phe
    220                 225                 230 gca gtg ctt gca gcg atg tgc att cta gct gtt cgg gca gta ata gtt        773
Ala Val Leu Ala Ala Met Cys Ile Leu Ala Val Arg Ala Val Ile Val
235                 240                 245                 250 caa ctt gca ttt ttc ctt cac atc cag act cat gta tac aag agg cca        821
Gln Leu Ala Phe Phe Leu His Ile Gln Thr His Val Tyr Lys Arg Pro
                255                 260                 265
```

```
cct gtc ttt tca aga tca ttg att ttt gct act gca ttc atg agc ttc      869
Pro Val Phe Ser Arg Ser Leu Ile Phe Ala Thr Ala Phe Met Ser Phe
        270                 275                 280 ttc tct gta gtt ata gca ctg ttt aag gat ata cct gac att gaa gga      917
Phe Ser Val Val Ile Ala Leu Phe Lys Asp Ile Pro Asp Ile Glu Gly
            285                 290                 295 gat aaa gta ttt ggc atc caa tct ttt tca gtg cgt tta ggt cag aag      965
Asp Lys Val Phe Gly Ile Gln Ser Phe Ser Val Arg Leu Gly Gln Lys
300                 305                 310 ccg gta ttc tgg act tgt gtt atc ctt ctt gaa ata gct tat gga gtc     1013
Pro Val Phe Trp Thr Cys Val Ile Leu Leu Glu Ile Ala Tyr Gly Val
315                 320                 325                 330 gcc ctc ctg gtg gga gct gca tct cct tgt ctt tgg agc aaa att gtc     1061
Ala Leu Leu Val Gly Ala Ala Ser Pro Cys Leu Trp Ser Lys Ile Val
                335                 340                 345 acg ggt ctg gga cac gct gtt ctg gct tca att ctc tgg ttt cat gcc     1109
Thr Gly Leu Gly His Ala Val Leu Ala Ser Ile Leu Trp Phe His Ala
            350                 355                 360 aaa tct gta gat ttg aaa agc aaa gct tcg ata aca tcc ttc tat atg     1157
Lys Ser Val Asp Leu Lys Ser Lys Ala Ser Ile Thr Ser Phe Tyr Met
        365                 370                 375 ttt att tgg aag cta ttt tat gca gaa tac tta ctc att cct ttt gtt     1205
Phe Ile Trp Lys Leu Phe Tyr Ala Glu Tyr Leu Leu Ile Pro Phe Val
    380                 385                 390 aga tga ggatgcagcg gcaatattga cttgagaatt agttttgttt aaatggtgct      1261
Arg *
395 gcctttgtca caggccggct tggagtcgct acattagttt taagttttta attgctaatt   1321 taaatgaaga tatatttctt ttgggatgaa aaaaaaaaa aaaaaaaa                 1370

<210> SEQ ID NO 22
<211> LENGTH: 395
<212> TYPE: PRT
<213> ORGANISM: Glycine max

<400> SEQUENCE: 22

Met Asp Ser Met Leu Leu Arg Ser Phe Pro Asn Ile Asn Asn Ala Ser
1               5                   10                  15

Ser Leu Ala Thr Thr Gly Ser Tyr Leu Pro Asn Ala Ser Trp His Asn
            20                  25                  30

Arg Lys Ile Gln Lys Glu Tyr Asn Phe Leu Arg Phe Arg Trp Pro Ser
        35                  40                  45

Leu Asn His His Tyr Lys Ser Ile Glu Gly Gly Cys Thr Cys Lys Lys
    50                  55                  60

Cys Asn Ile Lys Phe Val Val Lys Ala Thr Ser Glu Lys Ser Phe Glu
65                  70                  75                  80

Ser Glu Pro Gln Ala Phe Asp Pro Lys Ser Ile Leu Asp Ser Val Lys
                85                  90                  95

Asn Ser Leu Asp Ala Phe Tyr Arg Phe Ser Arg Pro His Thr Val Ile
            100                 105                 110

Gly Thr Ala Leu Ser Ile Ile Ser Val Ser Leu Leu Ala Val Glu Lys
        115                 120                 125

Ile Ser Asp Ile Ser Pro Leu Phe Phe Thr Gly Val Leu Glu Ala Val
    130                 135                 140

Val Ala Ala Leu Phe Met Asn Ile Tyr Ile Val Gly Leu Asn Gln Leu
145                 150                 155                 160

Ser Asp Val Glu Ile Asp Lys Ile Asn Lys Pro Tyr Leu Pro Leu Ala
```

```
                    165                 170                 175
Ser Gly Glu Tyr Ser Phe Glu Thr Gly Val Thr Ile Val Ala Ser Phe
                180                 185                 190

Ser Ile Leu Ser Phe Trp Leu Gly Trp Val Val Gly Ser Trp Pro Leu
            195                 200                 205

Phe Trp Ala Leu Phe Val Ser Phe Val Leu Gly Thr Ala Tyr Ser Ile
        210                 215                 220

Asn Val Pro Leu Leu Arg Trp Lys Arg Phe Ala Val Leu Ala Ala Met
225                 230                 235                 240

Cys Ile Leu Ala Val Arg Ala Val Ile Val Gln Leu Ala Phe Phe Leu
                245                 250                 255

His Ile Gln Thr His Val Tyr Lys Arg Pro Val Phe Ser Arg Ser
            260                 265                 270

Leu Ile Phe Ala Thr Ala Phe Met Ser Phe Ser Val Val Ile Ala
        275                 280                 285

Leu Phe Lys Asp Ile Pro Asp Ile Glu Gly Asp Lys Val Phe Gly Ile
        290                 295                 300

Gln Ser Phe Ser Val Arg Leu Gly Gln Lys Pro Val Phe Trp Thr Cys
305                 310                 315                 320

Val Ile Leu Leu Glu Ile Ala Tyr Gly Val Ala Leu Leu Val Gly Ala
                325                 330                 335

Ala Ser Pro Cys Leu Trp Ser Lys Ile Val Thr Gly Leu Gly His Ala
                340                 345                 350

Val Leu Ala Ser Ile Leu Trp Phe His Ala Lys Ser Val Asp Leu Lys
            355                 360                 365

Ser Lys Ala Ser Ile Thr Ser Phe Tyr Met Phe Ile Trp Lys Leu Phe
370                 375                 380

Tyr Ala Glu Tyr Leu Leu Ile Pro Phe Val Arg
385                 390                 395

<210> SEQ ID NO 23
<211> LENGTH: 1575
<212> TYPE: DNA
<213> ORGANISM: Glycine max
<220> FEATURE:
<221> NAME/KEY: CDS
<222> LOCATION: (109)...(1338)

<400> SEQUENCE: 23
cgaggagaga gagagaacta gtctcgagtt tagtctctac aatcactcct tcctctcatc     60
ctctataaag aaagtgctta atttgtgttg ttacttggtt cagtttcc atg gat tgg    117
                                                    Met Asp Trp
                                                      1 ggg ctt gct ata tct tct cat cct aaa cct tat tca gtc aca act ggt    165
Gly Leu Ala Ile Ser Ser His Pro Lys Pro Tyr Ser Val Thr Thr Gly
      5                  10                  15 gga aat ctc tgg cgg agt aaa cac acc acc aag aat att tac ttt gca    213
Gly Asn Leu Trp Arg Ser Lys His Thr Thr Lys Asn Ile Tyr Phe Ala
 20                  25                  30                  35 agt tct tgg ata tca aaa gct tca cga cac aaa agg gaa act caa ata    261
Ser Ser Trp Ile Ser Lys Ala Ser Arg His Lys Arg Glu Thr Gln Ile
                 40                  45                  50 gaa cat aat gtt ttg agg ttc caa caa cca agt ttg gat cat cat tac    309
Glu His Asn Val Leu Arg Phe Gln Gln Pro Ser Leu Asp His His Tyr
             55                  60                  65 aaa tgc atc aga gga ggg tct aca tat caa gaa tgc aat aga aaa ttt    357
Lys Cys Ile Arg Gly Gly Ser Thr Tyr Gln Glu Cys Asn Arg Lys Phe
```

```
          70              75              80
gtt gtg aag gca atc tct aaa caa cct ctt ggt ttt gaa gct cat gct      405
Val Val Lys Ala Ile Ser Lys Gln Pro Leu Gly Phe Glu Ala His Ala
         85              90              95 tcc aat cct aag aac att ttg gac tct gtc aaa aat gta ttg tct gct      453
Ser Asn Pro Lys Asn Ile Leu Asp Ser Val Lys Asn Val Leu Ser Ala
100             105             110             115 ttc tac tgg ttt tcc tat cca tac aca atg att ggc ata aca tta tgc      501
Phe Tyr Trp Phe Ser Tyr Pro Tyr Thr Met Ile Gly Ile Thr Leu Cys
                120             125             130 gca ttt tct tca tct ctt ctc gcg gtg gaa aaa tta tca gat ata tct      549
Ala Phe Ser Ser Ser Leu Leu Ala Val Glu Lys Leu Ser Asp Ile Ser
        135             140             145 tta tca ttt tta att ggc gtg tta cag ggt gtg ctg cct caa ttg ttt      597
Leu Ser Phe Leu Ile Gly Val Leu Gln Gly Val Leu Pro Gln Leu Phe
        150             155             160 att gaa att tat ctt tgt ggt gtg aat caa ctg tat gac ctt gaa ata      645
Ile Glu Ile Tyr Leu Cys Gly Val Asn Gln Leu Tyr Asp Leu Glu Ile
        165             170             175 gac aag ata aac aaa cca cat ctt cca atg gca tct gga caa ttt tcc      693
Asp Lys Ile Asn Lys Pro His Leu Pro Met Ala Ser Gly Gln Phe Ser
180             185             190             195 ttt aaa acc ggt gtc att att tct gca gca ttt tta gct ctg agt ttt      741
Phe Lys Thr Gly Val Ile Ile Ser Ala Ala Phe Leu Ala Leu Ser Phe
                200             205             210 gga ttt act tgg att acc ggc tct tgg cca ttg att tgt aat ctt gta      789
Gly Phe Thr Trp Ile Thr Gly Ser Trp Pro Leu Ile Cys Asn Leu Val
        215             220             225 gta atc gct tca tcg tgg acg gct tat tca atc gat gtg ccc cta ctg      837
Val Ile Ala Ser Ser Trp Thr Ala Tyr Ser Ile Asp Val Pro Leu Leu
        230             235             240 aga tgg aag aga tac cca ttt gtc gca gca atg tgc atg att tct act      885
Arg Trp Lys Arg Tyr Pro Phe Val Ala Ala Met Cys Met Ile Ser Thr
        245             250             255 tgg gct ctt gca ttg cca att tca tat ttc cat cac atg cag acc gtt      933
Trp Ala Leu Ala Leu Pro Ile Ser Tyr Phe His His Met Gln Thr Val
260             265             270             275 gtg ttg aag agg cca att ggc ttt cca aga tca ttg ggt ttt ctt gtt      981
Val Leu Lys Arg Pro Ile Gly Phe Pro Arg Ser Leu Gly Phe Leu Val
                280             285             290 gca ttc atg acc ttc tac tcc ttg ggt ttg gca ttg tcc aag gat ata     1029
Ala Phe Met Thr Phe Tyr Ser Leu Gly Leu Ala Leu Ser Lys Asp Ile
        295             300             305 cct gac gtt gaa gga gat aaa gag cac ggc att gat tct ttt gca gta     1077
Pro Asp Val Glu Gly Asp Lys Glu His Gly Ile Asp Ser Phe Ala Val
        310             315             320 cgt cta ggt cag aaa cgg gca ttt tgg att tgc gtt tcc ttt ttt gaa     1125
Arg Leu Gly Gln Lys Arg Ala Phe Trp Ile Cys Val Ser Phe Phe Glu
325             330             335 atg gct ttc gga gtt ggt atc ctg gcc gga gca tca tgc tca cac ttt     1173
Met Ala Phe Gly Val Gly Ile Leu Ala Gly Ala Ser Cys Ser His Phe
340             345             350             355 tgg act aaa att ttc acg ggt atg gga aat gct gtt ctt gct tca att     1221
Trp Thr Lys Ile Phe Thr Gly Met Gly Asn Ala Val Leu Ala Ser Ile
                360             365             370 ctc tgg tac caa gcc aag tcc gta gat ttg agc gac aaa gct tcc act     1269
Leu Trp Tyr Gln Ala Lys Ser Val Asp Leu Ser Asp Lys Ala Ser Thr
        375             380             385 gga tct ttc tat atg ttc atc tgg aag cta ttg tat gca ggg ttc ttt     1317
```

```
Gly Ser Phe Tyr Met Phe Ile Trp Lys Leu Leu Tyr Ala Gly Phe Phe
        390                 395                 400 ctc atg gca tta att aga tga ggatatcgtg gaaggcttaa acaatgttct      1368
Leu Met Ala Leu Ile Arg  *
    405 cgacacatac accaaaataa aaggaatata tgttttgcat ctaagattta ttaaataaag  1428 ccgaatgttg gttcttgtat cattaagatt ttttttttaa ttgtcgaaga ctttatgtat  1488 tcatattcac cttgacttct acggtcaaat ttttcataaa gtggaataaa agcaacttgg  1548 tatacaaaaa aaaaaaaaaa aaaaaaa                                      1575
```

<210> SEQ ID NO 24
<211> LENGTH: 409
<212> TYPE: PRT
<213> ORGANISM: Glycine max

<400> SEQUENCE: 24

```
Met Asp Trp Gly Leu Ala Ile Ser Ser His Pro Lys Pro Tyr Ser Val
 1               5                   10                  15

Thr Thr Gly Gly Asn Leu Trp Arg Ser Lys His Thr Thr Lys Asn Ile
            20                  25                  30

Tyr Phe Ala Ser Ser Trp Ile Ser Lys Ala Ser Arg His Lys Arg Glu
        35                  40                  45

Thr Gln Ile Glu His Asn Val Leu Arg Phe Gln Gln Pro Ser Leu Asp
    50                  55                  60

His His Tyr Lys Cys Ile Arg Gly Gly Ser Thr Tyr Gln Glu Cys Asn
65                  70                  75                  80

Arg Lys Phe Val Val Lys Ala Ile Ser Lys Gln Pro Leu Gly Phe Glu
                85                  90                  95

Ala His Ala Ser Asn Pro Lys Asn Ile Leu Asp Ser Val Lys Asn Val
            100                 105                 110

Leu Ser Ala Phe Tyr Trp Phe Ser Tyr Pro Tyr Thr Met Ile Gly Ile
        115                 120                 125

Thr Leu Cys Ala Phe Ser Ser Ser Leu Leu Ala Val Glu Lys Leu Ser
    130                 135                 140

Asp Ile Ser Leu Ser Phe Leu Ile Gly Val Leu Gln Gly Val Leu Pro
145                 150                 155                 160

Gln Leu Phe Ile Glu Ile Tyr Leu Cys Gly Val Asn Gln Leu Tyr Asp
                165                 170                 175

Leu Glu Ile Asp Lys Ile Asn Lys Pro His Leu Pro Met Ala Ser Gly
            180                 185                 190

Gln Phe Ser Phe Lys Thr Gly Val Ile Ile Ser Ala Ala Phe Leu Ala
        195                 200                 205

Leu Ser Phe Gly Phe Thr Trp Ile Thr Gly Ser Trp Pro Leu Ile Cys
    210                 215                 220

Asn Leu Val Val Ile Ala Ser Ser Trp Thr Ala Tyr Ser Ile Asp Val
225                 230                 235                 240

Pro Leu Leu Arg Trp Lys Arg Tyr Pro Phe Val Ala Ala Met Cys Met
                245                 250                 255

Ile Ser Thr Trp Ala Leu Ala Leu Pro Ile Ser Tyr Phe His His Met
            260                 265                 270

Gln Thr Val Val Leu Lys Arg Pro Ile Gly Phe Pro Arg Ser Leu Gly
        275                 280                 285

Phe Leu Val Ala Phe Met Thr Phe Tyr Ser Leu Gly Leu Ala Leu Ser
    290                 295                 300
```

```
Lys Asp Ile Pro Asp Val Glu Gly Asp Lys Glu His Gly Ile Asp Ser
305                 310                 315                 320

Phe Ala Val Arg Leu Gly Gln Lys Arg Ala Phe Trp Ile Cys Val Ser
                325                 330                 335

Phe Phe Glu Met Ala Phe Gly Val Gly Ile Leu Ala Gly Ala Ser Cys
            340                 345                 350

Ser His Phe Trp Thr Lys Ile Phe Thr Gly Met Gly Asn Ala Val Leu
        355                 360                 365

Ala Ser Ile Leu Trp Tyr Gln Ala Lys Ser Val Asp Leu Ser Asp Lys
370                 375                 380

Ala Ser Thr Gly Ser Phe Tyr Met Phe Ile Trp Lys Leu Leu Tyr Ala
385                 390                 395                 400

Gly Phe Phe Leu Met Ala Leu Ile Arg
                405

<210> SEQ ID NO 25
<211> LENGTH: 368
<212> TYPE: DNA
<213> ORGANISM: Triticum aestivum
<220> FEATURE:
<221> NAME/KEY: CDS
<222> LOCATION: (1)...(363)

<400> SEQUENCE: 25 gca aca ttg ttc atg tgt tgc ttc tct gcc gtc ata gct cta ttc aag      48
Ala Thr Leu Phe Met Cys Cys Phe Ser Ala Val Ile Ala Leu Phe Lys
1               5                   10                  15 gat att cct gat gtt gat gga gac cga gat ttt ggc atc caa tcc ttg      96
Asp Ile Pro Asp Val Asp Gly Asp Arg Asp Phe Gly Ile Gln Ser Leu
                20                  25                  30 agt gtg aga ttg ggg cca caa aga gtg tat cag ctc tgc ata agc ata     144
Ser Val Arg Leu Gly Pro Gln Arg Val Tyr Gln Leu Cys Ile Ser Ile
            35                  40                  45 ctg tta aca gcc tat ggg gct gcc act gta gta gga gct tca tcc aca     192
Leu Leu Thr Ala Tyr Gly Ala Ala Thr Val Val Gly Ala Ser Ser Thr
        50                  55                  60 cac cta ctt caa aag atc atc act gtg tct ggc cat ggc ctg ctt gct     240
His Leu Leu Gln Lys Ile Ile Thr Val Ser Gly His Gly Leu Leu Ala
65                  70                  75                  80 gtg aca ctt tgg cag aga gcg cgg cac ctt gag gtt gaa aac caa gcg     288
Val Thr Leu Trp Gln Arg Ala Arg His Leu Glu Val Glu Asn Gln Ala
                85                  90                  95 cgt gtc aca tca ttt tac atg ttc att tgg aag cta ttc tat gca aag     336
Arg Val Thr Ser Phe Tyr Met Phe Ile Trp Lys Leu Phe Tyr Ala Lys
            100                 105                 110 tat ttc ctt ata ccg ttt gtg caa taa aattt                           368
Tyr Phe Leu Ile Pro Phe Val Gln *
        115                 120

<210> SEQ ID NO 26
<211> LENGTH: 120
<212> TYPE: PRT
<213> ORGANISM: Triticum aestivum

<400> SEQUENCE: 26

Ala Thr Leu Phe Met Cys Cys Phe Ser Ala Val Ile Ala Leu Phe Lys
1               5                   10                  15

Asp Ile Pro Asp Val Asp Gly Asp Arg Asp Phe Gly Ile Gln Ser Leu
                20                  25                  30
```

```
Ser Val Arg Leu Gly Pro Gln Arg Val Tyr Gln Leu Cys Ile Ser Ile
        35                  40                  45

Leu Leu Thr Ala Tyr Gly Ala Ala Thr Val Val Gly Ala Ser Ser Thr
50                  55                  60

His Leu Leu Gln Lys Ile Ile Thr Val Ser Gly His Gly Leu Leu Ala
65                  70                  75                  80

Val Thr Leu Trp Gln Arg Ala Arg His Leu Glu Val Glu Asn Gln Ala
                85                  90                  95

Arg Val Thr Ser Phe Tyr Met Phe Ile Trp Lys Leu Phe Tyr Ala Lys
            100                 105                 110

Tyr Phe Leu Ile Pro Phe Val Gln
        115                 120

<210> SEQ ID NO 27
<211> LENGTH: 1477
<212> TYPE: DNA
<213> ORGANISM: Triticum asestivum
<220> FEATURE:
<221> NAME/KEY: CDS
<222> LOCATION: (20)...(1171)

<400> SEQUENCE: 27
cacgagcccc tccccaccc atg gct tcc ctc gcc tcc cct ccc gtc ccc tcc         52
                    Met Ala Ser Leu Ala Ser Pro Pro Val Pro Ser
                     1               5                  10 cac gcg ccc acc acc gcc gct cgc ttc ctc ccc gcg ccg gcc ggc cgc         100
His Ala Pro Thr Thr Ala Ala Arg Phe Leu Pro Ala Pro Ala Gly Arg
            15                  20                  25 ggc agg cgc ccg tcg ccg ccg gcc gct tca cct atc ttc tcc tct gct         148
Gly Arg Arg Pro Ser Pro Pro Ala Ala Ser Pro Ile Phe Ser Ser Ala
        30                  35                  40 tcc acc cga ttc acc cag tcc ccg cgc gcc ccc tgc ggc gcc gcc cga         196
Ser Thr Arg Phe Thr Gln Ser Pro Arg Ala Pro Cys Gly Ala Ala Arg
    45                  50                  55 ccg cgc tgg cgc gac acc gtg cgg gca tgc tct caa gct ggt gca gct         244
Pro Arg Trp Arg Asp Thr Val Arg Ala Cys Ser Gln Ala Gly Ala Ala
60                  65                  70                  75 ggg cca gct cca ctg tca aag aca tta tca gac cta aag gat tcc tgc         292
Gly Pro Ala Pro Leu Ser Lys Thr Leu Ser Asp Leu Lys Asp Ser Cys
                80                  85                  90 tgg aga ttt tta agg cca cac aca att cgt gga act gct ttg gga tcc         340
Trp Arg Phe Leu Arg Pro His Thr Ile Arg Gly Thr Ala Leu Gly Ser
            95                 100                 105 aca gcc ttg gtt gct aga gca tta tta gag aat ccc caa ttg atc gat         388
Thr Ala Leu Val Ala Arg Ala Leu Leu Glu Asn Pro Gln Leu Ile Asp
        110                 115                 120 tgg cgc ttg gta ttc aaa gca tta tat ggc ctt gta gct ttg atc tgc         436
Trp Arg Leu Val Phe Lys Ala Leu Tyr Gly Leu Val Ala Leu Ile Cys
    125                 130                 135 ggc aac ggt tac att gtt ggg att aat cag atc tat gac att gga att         484
Gly Asn Gly Tyr Ile Val Gly Ile Asn Gln Ile Tyr Asp Ile Gly Ile
140                 145                 150                 155 gac aag gta aac aaa cca tat tta cct att gct gcc ggt gat ctc tca         532
Asp Lys Val Asn Lys Pro Tyr Leu Pro Ile Ala Ala Gly Asp Leu Ser
                160                 165                 170 gtt cag tca gca tgg tta ctg gtc gta gca ttc gca gtg gtg ggc ttc         580
Val Gln Ser Ala Trp Leu Leu Val Val Ala Phe Ala Val Val Gly Phe
            175                 180                 185 tca ata gtc gtt tca aac ttt gga cct ttc atc acc tct ctt tac tgc         628
Ser Ile Val Val Ser Asn Phe Gly Pro Phe Ile Thr Ser Leu Tyr Cys
```

```
                190                 195                 200
ctt ggt cta ttt ctt ggc act ata tat tct gtt cct cca ttc aga ctg      676
Leu Gly Leu Phe Leu Gly Thr Ile Tyr Ser Val Pro Pro Phe Arg Leu
        205                 210                 215 aag aga tat cca gtt gct gct ttt ctt atc att gcg acg gtt cgt gga      724
Lys Arg Tyr Pro Val Ala Ala Phe Leu Ile Ile Ala Thr Val Arg Gly
220                 225                 230                 235 ttc ctt ctc aac ttt ggg gtg tac tat gct act aga gct gca tta ggt      772
Phe Leu Leu Asn Phe Gly Val Tyr Tyr Ala Thr Arg Ala Ala Leu Gly
                240                 245                 250 ctt aca ttc caa tgg agc tcg ccc gtt gct ttt att aca tgc ttt gtg      820
Leu Thr Phe Gln Trp Ser Ser Pro Val Ala Phe Ile Thr Cys Phe Val
        255                 260                 265 aca gta ttt gct ctg gtc att gct ata acc aaa gat ctt ccg gat gtt      868
Thr Val Phe Ala Leu Val Ile Ala Ile Thr Lys Asp Leu Pro Asp Val
270                 275                 280 gaa ggg gac cgc aaa ttc caa ata tca act ttg gcg aca aag ctt ggt      916
Glu Gly Asp Arg Lys Phe Gln Ile Ser Thr Leu Ala Thr Lys Leu Gly
        285                 290                 295 gtc aga aat att gcc ttc ctt ggc tct ggt tta ttg ttg gca aat tat      964
Val Arg Asn Ile Ala Phe Leu Gly Ser Gly Leu Leu Leu Ala Asn Tyr
300                 305                 310                 315 gtt gtt gct att gta gta cct ttt ctt att cct cag gct ttc agg agc     1012
Val Val Ala Ile Val Val Pro Phe Leu Ile Pro Gln Ala Phe Arg Ser
                320                 325                 330 ttt gta atg gtg cct ttt cat gct gct ctt gca gtt gct tta att ttt     1060
Phe Val Met Val Pro Phe His Ala Ala Leu Ala Val Ala Leu Ile Phe
        335                 340                 345 cag aca tgg gtt ctg gag caa gca aag tac agt aag gat gct att tca     1108
Gln Thr Trp Val Leu Glu Gln Ala Lys Tyr Ser Lys Asp Ala Ile Ser
350                 355                 360 cag tac tac cgg ttc atc tgg aac ctc ttc tat gcc gaa tac atc ttc     1156
Gln Tyr Tyr Arg Phe Ile Trp Asn Leu Phe Tyr Ala Glu Tyr Ile Phe
        365                 370                 375 ttc ccg tta ata tag agatatggcg tttgacatcg gctacacgat cggagcacgc     1211
Phe Pro Leu Ile *
380 accgaagcac gaattcgttg gggcaacaga agagaaaccc tttgtggtct ataaagcgtg    1271 agcaattttt gtacatactg tttgactggt aggggaatag agcggcgatg cgacgaggat    1331 cttgacgatg ctgtgggagg atccagtaga aaatgactga gttttcgtgg ttgtttctgc    1391 caaacaaaga ggaaagaaa  tgaaagtgaa aaggtatcgg gccttgtttt ggagggattg    1451 gacgtaaaaa aaaaaaaaaa aaaaca                                         1477

<210> SEQ ID NO 28
<211> LENGTH: 383
<212> TYPE: PRT
<213> ORGANISM: Triticum asestivum

<400> SEQUENCE: 28

Met Ala Ser Leu Ala Ser Pro Pro Val Pro Ser His Ala Pro Thr Thr
1               5                   10                  15

Ala Ala Arg Phe Leu Pro Ala Pro Ala Gly Arg Gly Arg Pro Ser
            20                  25                  30

Pro Pro Ala Ala Ser Pro Ile Phe Ser Ser Ala Ser Thr Arg Phe Thr
        35                  40                  45

Gln Ser Pro Arg Ala Pro Cys Gly Ala Ala Arg Pro Arg Trp Arg Asp
50                  55                  60
```

```
Thr Val Arg Ala Cys Ser Gln Ala Gly Ala Ala Gly Pro Ala Pro Leu
 65                  70                  75                  80

Ser Lys Thr Leu Ser Asp Leu Lys Asp Ser Cys Trp Arg Phe Leu Arg
                 85                  90                  95

Pro His Thr Ile Arg Gly Thr Ala Leu Gly Ser Thr Ala Leu Val Ala
                100                 105                 110

Arg Ala Leu Leu Glu Asn Pro Gln Leu Ile Asp Trp Arg Leu Val Phe
            115                 120                 125

Lys Ala Leu Tyr Gly Leu Val Ala Leu Ile Cys Gly Asn Gly Tyr Ile
        130                 135                 140

Val Gly Ile Asn Gln Ile Tyr Asp Ile Gly Ile Asp Lys Val Asn Lys
145                 150                 155                 160

Pro Tyr Leu Pro Ile Ala Ala Gly Asp Leu Ser Val Gln Ser Ala Trp
                165                 170                 175

Leu Leu Val Val Ala Phe Ala Val Val Gly Phe Ser Ile Val Val Ser
                180                 185                 190

Asn Phe Gly Pro Phe Ile Thr Ser Leu Tyr Cys Leu Gly Leu Phe Leu
            195                 200                 205

Gly Thr Ile Tyr Ser Val Pro Pro Phe Arg Leu Lys Arg Tyr Pro Val
        210                 215                 220

Ala Ala Phe Leu Ile Ile Ala Thr Val Arg Gly Phe Leu Leu Asn Phe
225                 230                 235                 240

Gly Val Tyr Tyr Ala Thr Arg Ala Ala Leu Gly Leu Thr Phe Gln Trp
                245                 250                 255

Ser Ser Pro Val Ala Phe Ile Thr Cys Phe Val Thr Val Phe Ala Leu
                260                 265                 270

Val Ile Ala Ile Thr Lys Asp Leu Pro Asp Val Glu Gly Asp Arg Lys
            275                 280                 285

Phe Gln Ile Ser Thr Leu Ala Thr Lys Leu Gly Val Arg Asn Ile Ala
        290                 295                 300

Phe Leu Gly Ser Gly Leu Leu Leu Ala Asn Tyr Val Val Ala Ile Val
305                 310                 315                 320

Val Pro Phe Leu Ile Pro Gln Ala Phe Arg Ser Val Met Val Pro
                325                 330                 335

Phe His Ala Ala Leu Ala Val Ala Leu Ile Phe Gln Thr Trp Val Leu
            340                 345                 350

Glu Gln Ala Lys Tyr Ser Lys Asp Ala Ile Ser Gln Tyr Tyr Arg Phe
        355                 360                 365

Ile Trp Asn Leu Phe Tyr Ala Glu Tyr Ile Phe Phe Pro Leu Ile
370                 375                 380

<210> SEQ ID NO 29
<211> LENGTH: 473
<212> TYPE: DNA
<213> ORGANISM: Triticum aestivum
<220> FEATURE:
<221> NAME/KEY: intron
<222> LOCATION: (322)...(426)

<400> SEQUENCE: 29
gcaacattgt tcatgtgttg cttctctgcc gtcatagctc tattcaagga tattcctgat    60
gttgatggag accgagattt tggcatccaa tccttgagtg tgagattggg gccacaaaga   120
gtgtatcagc tctgcataag catactgtta acagcctatg gggctgccac tgtagtagga   180
gcttcatcca cacacctact tcaaaagatc atcactgtgt ctggccatgg cctgcttgct   240
```

```
gtgacacttt ggcagagagc gcggcacctt gaggttgaaa accaagcgcg tgtcacatca      300
ttttacatgt tcatttggaa ggtaactaat taagttgctc gcatatattg tgcattctct      360
aagccattaa actttggcta tatatgccta atgattattt gcacttattg tgtcactttc      420
atgcagctat tctatgcaaa gtatttcctt ataccgtttg tgcaataaaa ttt             473

<210> SEQ ID NO 30
<211> LENGTH: 21
<212> TYPE: DNA
<213> ORGANISM: Artificial Sequence
<220> FEATURE:
<223> OTHER INFORMATION: PCR primer

<400> SEQUENCE: 30
gacatatttt tgcagtctgc c                                                 21

<210> SEQ ID NO 31
<211> LENGTH: 36
<212> TYPE: DNA
<213> ORGANISM: Artificial Sequence
<220> FEATURE:
<223> OTHER INFORMATION: PCR primer

<400> SEQUENCE: 31
agcgcggccg catggacgcg cttcgcctac ggccgt                                 36

<210> SEQ ID NO 32
<211> LENGTH: 35
<212> TYPE: DNA
<213> ORGANISM: Artificial Sequence
<220> FEATURE:
<223> OTHER INFORMATION: PCR primer

<400> SEQUENCE: 32
agcgcggccg ctcaccgcac cagagggatg agcag                                  35
```

PHYTYL/PRENYLTRANSFERASE NUCLEIC ACIDS, POLYPEPTIDES AND USES THEREOF

CROSS-REFERENCE TO RELATED APPLICATIONS

This application is a CIP of U.S. patent application Ser. No. 09/307,460 filed May 7, 1999, now abandoned which is hereby incorporated by reference.

TECHNICAL FIELD

The present invention relates generally to plant molecular biology. More specifically, it relates to nucleic acids and methods for modulating their expression in plants.

BACKGROUND OF THE INVENTION

The chloroplasts of higher plants contain and elaborate many unique, interconnected biochemical pathways that produce an array of compounds that not only perform vital plastid functions but are also important from agricultural and nutritional perspectives. One class of lipid soluble, chloroplastically synthesized compounds are the prenyllipids, plastoquinone and tocopherols. Plastoquinone is a fundamentally important component of the chloroplast photosynthetic electron transport chain and accounts for up to 50% of the total prenyllipid pool in green tissues. Tocopherols collectively account for up to 40% of the total prenyllipids pool in green plastids and have a well documented role in mammals as an antioxidant [Liebler, 1993] and a similar, though less well understood antioxidant role in plants [Hess, 1993]. The essential nutritional value of tocopherols has been known for over 70 years [Mason, 1980]. Despite the well studied, wide-spread importance of these chloroplastic compounds to human nutrition, agriculture and biochemical processes within plant cells, much remains to be learned at the molecular level about their biosynthesis.

Plastoquinone and tocopherols are the most abundant prenyllipids in the plastid and are synthesized by the common pathway reviewed in Hess, 1993 and Soll, 1987. The head group for both compounds, homogentisic acid, is produced from p-hydroxyphenylpyruvic acid by the enzyme p-hydroxyphenylpyruvic acid dioxygenase in a reaction that catalyzes both an oxidation and decarboxylation. Homogentisic acid is subject to phytylation/prenylation (phytyl and solanyl, C20 and C45, respectively) coupled to a simultaneous decarboxylation to form the first true tocopherol and plastoquinone intermediates, 2-demethyl-phytylplastoquinol and 2-demethylplastoquinol-9, respectively. A single ring methylation occurs on 2-demethylplastoquinol to yield plastoquinol-9 that is then oxidized to plastoquinone-9. The preferred route in spinach for α-tocopherol formation is thought to be 1) ring methylation of 2-demethylphytylplastoquinol, to yield phytylplastoquinol, 2) cyclization to yield gamma-tocopherol and, finally, 3) a second ring methylation to yield α-tocopherol. The first ring methylation in both tocopherol and plastoquinone synthesis is thought to be carried out by a single enzyme that is specific for the sight of methylation on the ring but has broad substrate specificity and accommodates both classes of compounds. The final methylation enzyme (gamma tocopherol methyl transferase) is the only enzyme of the pathway that has been purified from plants to date (dHarlingue and Camara, 1985). All other enzymatic activities of tocopherol/plastoquinone synthesis have been localized to the inner chloroplast envelope by fractionation studies except p-hydroxyphenylpyruvic acid dioxygenase and the tocopherol cyclase enzyme. Difficulties with cell fractionation methods, low activities for some of the enzymes, substrate stability and availability and assay problems make studying the pathway biochemically extremely challenging.

The fact that tocopherol and plastoquinone levels, ratios and total amounts vary by orders of magnitude in different plant tissues and developmental stages indicates the pathway is both highly regulated and highly flexible and has potential for quantitative and qualitative manipulation. However, while biochemical analysis has been useful in deciphering the biosynthetic pathway such studies have provided almost no insight into how bulk carbon flow through the pathway is regulated or how differing amounts of tocopherols or plastoquinone are synthesized.

SUMMARY OF THE INVENTION

It is an object of the present invention to provide nucleic acids and polypeptides relating to the biosynthesis of tocopherol and plastiquinone.

It is another object of the present invention to provide nucleic acids and polypeptides that can be used to identify proteins involved in tocopherol and plastiquinone biosynthesis.

It is another object of the present invention to provide antgenic fragments of the polypeptides of the present invention.

It is another object of the present invention to provide transgenic plants comprising the nucleic acids of the present invention.

It is another object of the present invention to provide methods for modulating, in a transgenic plant, the expression of the nucleic acids of the present invention.

It is another object of the present invention to provide a method for modulating the level of tocopherols and plastiquinone in a plant.

Other aspects of the present invention include expression cassettes comprising the nucleic acid operably linked to a promoter, host cells transfected with the expression cassette, and transgenic plants and seeds comprising the expression cassette.

In a further aspect, the present invention relates to a method of modulating expression of the nucleic acids in a plant, comprising the steps of (a) transforming a plant cell with an expression cassette comprising a nucleic acid of the present invention operably linked to a promoter in sense or antisense orientation;

(b) growing the plant cell under plant growing conditions to produce a regenerated plant capable of expressing the nucleic acid for a time sufficient to modulate expression of the nucleic acids in the plant compared to a corresponding non-transformed plant.

Expression of the nucleic acids encoding the proteins of the present invention can be increased or decreased relative to a non-transformed control plant.

DETAILED DESCRIPTION OF THE INVENTION

Tocopherols are synthesized in the inner plastid membrane. The first committed step in the pathway is the condensation of the homogentisate head group with the phytyl tail catalyzed by an integral membrane protein: homogentisate: phytyl transferase. The present polypeptides catalyze the condensation of homogentisic acid with phytyldiphosphate or geranylgeranyl pyrophosphate to produce the first intermediates in tocopherol or tocotrienol synthesis, respectively.

The phytylation/prenylation of homogentisic acid is a likely key regulatory step for "tail" synthesis and in determining the relative amounts of tocopherols, tocotrienols and plastoquinone produced as it is the branchpoint for the tocopherol and plastoquinone arms of the pathway.

One purpose of this invention is to modulate a prenyllipid biosynthetic pathway, such as the plastoquinone and tocopherol pathways. The modulation of the pathway may be an up regulation or down regulation of the amount or activity of a prenyllipid (ie. plastoquinone or tocopherol), or of an intermediate in a pathway (ie. 2-demethylphytylplastoquinol or 2-demethylplastoquinol-9).

Definitions

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

The terms polypeptide, "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of the protein of the invention.

As used herein, "plant" includes but is not limited to plant cells, plant tissue and plant seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Preferably fragments of a nucleotide sequence may encode protein fragments that retain the biological activity of the native nucleic acid. However, fragments of a nucleotide sequence which are useful as hybridization probes generally do not encode fragment proteins retaining biological activity. Fragments of a nucleotide sequence are generally greater than 10 nucleotides, preferably at least 20 nucleotides and up to the entire nucleotide sequence encoding the proteins of the invention. Generally probes are less than 1000 nucleotides and preferably less than 500 nucleotides. Fragments of the invention include antisense sequences used to decrease expression of the inventive nucleic acids. Such antisense fragments may vary in length ranging from at least about 20 nucleotides, about 50 nucleotides, about 100 nucleotides, up to and including the entire coding sequence.

By "variants" is intended substantially similar sequences. Generally, nucleic acid sequence variants of the invention will have at least 50%, 60%, 70%, or preferably 80%, more preferably at least 90% and most preferably at least 95% sequence identity to the native nucleotide sequence.

Generally, polypeptide sequence variants of the invention will have at least about 55%, 60%, 70%, 80%, or preferably at least about 90% and more preferably at least about 95% sequence identity to the native protein.

As used herein, "sequence identity" or "identity" in the context of two nucleic acid or polypeptide sequences includes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ for conservative substitutions, the percent identity may be adjusted upward to correct for the conservative nature of the substitution. Means for making this adjustment are well known to those skilled in the art, and typically involve scoring a conservative substitution as a partial rather than a full mismatch.

Methods of alignment of sequences for comparison are well-known in the art. Two methods are used herein to define the present invention. The first is the BLAST 2.0 suite of programs using default parameters. Altschul et al., *Nucleic Acids Res.* 25:3389–3402 (1997). Software for performing BLAST analyses is publicly available, e.g., through the National Center for Biotechnology Information. The second is the GAP program, available as part of the Wisconsin Genetics Software Package, that uses the algorithm of Needleman and Wunsch (*J. Mol. Biol.* 48:443–453, 1970) to find the alignment of two complete sequences that maximizes the number of matches and minimizes the number of gaps. Default gap creation penalty values and gap extension penalty values in Version 10 of the Wisconsin Genetics Software Package for nucleotide sequences are 50 and 3, respectively, and for protein sequences are 8 and 2, respectively. Unless otherwise specified, references to the GAP program or algorithm refer to the GAP program or algorithm in version 10 of the Wisconsin Genetics Software Package. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater. The scoring matrix used in Version 10 of the Wisconsin Genetics Software Package is BLOSUM62 (see Henikoff & Henikoff (1989) *Proc. Natl. Acad. Sci. USA* 89:10915).

When GAP is used to compute % sequence identities for sequences of differing length, results determined by GAP may be reduced for non-overlapping nucleotides or amino acids in the longer sequence. For example, if a sequence of 100 is compared to a sequence of 40, GAP may determine the percent identity to be 100% if the 40 nucleotides or amino acids of the shorter sequence match 40 nucleotides or amino acids of the larger sequence. This is because GAP may calculate the percent identity based on the total length of the shorter sequence. However, where this specification, including the claims, specifies the sequence identity being computed by GAP, the GAP percentage identity should be re-calculated as a percentage of the longer sequence and any nucleotides or amino acids in the larger sequence that extend beyond the shorter sequence would not count as a match. In the example provided above this would give a percent identity of 40%.

Other methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, FASTA, BLAST and TFASTA in the Wisconsin Genetics Software Package, Genetics Computer Group (GCG), 575 Science Dr., Madison, Wis., USA; the CLUSTAL program is well described by Higgins and Sharp, Gene 73:237–244 (1988); Higgins and Sharp, CABIOS 5:151–153 (1989); Corpet et al., Nucleic Acids Research 16:10881–90 (1988); Huang et al., Computer Applications in the Biosciences 8:155–65 (1992), and Pearson et al., Methods in Molecular Biology 24:307–331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See Current Protocols in Molecular Biology, Chapter 19, Ausubel et al., Eds., Greene Publishing and Wiley-lnterscience, New York (1995). Software for performing BLAST analyses is publicly available, e.g., through the National Center for Biotechnology Information (http://www.ncbi.nlm.nih.gov/). The BLAST algorithm performs a statistical analysis of the similarity between two sequences (see, e.g., Karlin & Altschul, Proc. Nat'l. Acad. Sci. USA 90:5873–5877 (1993)). One measure of similarity provided by the BLAST algorithm is the smallest sum probability (P(N)), which provides an indication of the probability by which a match between two nucleotide or amino acid sequences would occur by chance.

The term "functional equivalent" means that the sequence of the variant polynucleotide defines a chain that produces a protein having substantially the same biological effect as the protein encoded by the non-variant polynucleotide.

The term "Complement" or "Complementary" when used with respect to a polynucleotide sequence refers to the corresponding base pairs in the same sequence.

The term "Hybridizabon Probe" refers to a process whereby a polynucleotide is used to find a complementary polynucloetide through the annealing of the two polynucleotides to form a double helix.

The term "Coding Sequence" when used with respect to a complete gene sequence refers to the sequence spanning the start and stop codon, and when used with respect to a partial gene sequence refers to a portion of the coding region spanning the start and stop codon.

Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot or dicot. In preferred embodiments the monocot is corn, sorghum, barley, wheat, millet, or rice. Preferred dicots include soybeans, sunflower, canola, alfalfa, cotton, potato, cassava, Arabidopsis thaliana, tomato, Brassica vegetables, peppers, potatoes, apples, spinach, or lettuce.

Functional fragments included in the invention can be obtained using primers that selectively hybridize under stringent conditions. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), DIRECTED MUTAGENESIS: A Practical approach, (IRL Press, 1991). Thus, the present invention also encompasses DNA molecules comprising nucleotide sequences that have substantial sequence identity with the inventive sequences.

Variants included in the invention may contain individual substitutions, deletions or additions to the nucleic acid or polypeptide sequences. Such changes will alter, add or delete a single amino acid or a small percentage of amino acids in the encoded sequence. Variants are referred to as "conservatively modified variants" where the alteration results in the substitution of an amino acid with a chemically similar amino acid. When the nucleic acid is prepared or altered synthetically, advantage can be taken of known codon preferences of the intended host.

The present invention also includes "shufflents" produced by sequence shuffling of the inventive polynucleotides to obtain a desired characteristic. Sequence shuffling is described in PCT publication No. 96/19256. See also, Zhang, J. H., et al., Proc. Natl. Acad. Sci. USA 94:4504–4509 (1997).

The present invention also includes the use of 5' and/or 3' UTR regions for modulation of translation of heterologous coding sequences. Positive sequence motifs include translational initiation consensus sequences (Kozak, Nucleic Acids Res. 15:8125 (1987)) and the 7-methylguanosine cap structure (Drummond et al., Nucleic Acids Res. 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, supra, Rao et al., Mol. and Cell. Biol. 8:284 (1988)).

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387–395 (1984)) or MacVector 4.1 (Eastman Kodak Co., New Haven, Conn.).

For example, the inventive nucleic acids can be optimized for enhanced expression in organisms of interest. See, for example, EPA0359472; WO91/16432; Perlak et al., *Proc. Natl. Acad. Sci. USA* 88:3324–3328 (1991); and Murray et al., *Nucleic Acids Res.* 17:477–498 (1989). In this manner, the genes can be synthesized utilizing species-preferred codons. See, for example, Murray et al., *Nucleic Acids Res.* 17:477–498 (1989), the disclosure of which is incorporated herein by reference.

The present invention provides subsequences comprising isolated nucleic acids containing at least 16 contiguous bases of the inventive sequences. For example the isolated nucleic acid includes those comprising at least 20, 25, 30, 40, 50, 60, 75 or 100 or more contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library.

Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-lnterscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253.

Typical cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-lnterscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics* 37:327–336 (1996). Other methods for producing full-length libraries are known in the art. See, e.g., Edery et al., *Mol. Cell Biol.* 15(6):3363–3371 (1995); and, PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.* 18(19):5705–5711 (1990); Patanjali et al., *Proc. Natl. Acad. USA* 88:1943–1947 (1991); U.S. Pat. Nos. 5,482,685 and 5,637,685; and Soares et al., *Proc. Natl. Acad. Sci. USA* 91:9228–9232 (1994).

Subtracted cDNA libraries are another means to increase the proportion of less abundant cDNA species. See, Foote et al. in, *Plant Molecular Biology: A Laboratory Manual*, Clark, Ed., Springer-Verlag, Berlin (1997); Kho and Zarbl, Technique, 3(2):58–63 (1991); Sive and St. John, *Nucl. Acids Res.* 16(22):10937 (1988); *Current Protocols in Molecular Biology*, Ausubel, et al., Eds., Greene Publishing and Wiley-Interscience, New York (1995); and, Swaroop et al., *Nucl. Acids Res.* 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Typically the hybridization will be conducted for about 4 to about 12 hours.

Preferably the hybridization is conducted under low stringency conditions which include hybridization with a buffer solution of 30% formamide, 1 M NaCl, 1% SDS (sodium dodecyl sulfate) at 37° C., and a wash in 1× to 2×SSC (20×SSC =3.0 M NaCl/0.3 M trisodium citrate) at 50° C. More preferably the hybridization is conducted under moderate stringency conditions which include hybridization in 40% formamide, 1 M NaCl, 1% SDS at 37° C., and a wash in 0.5× to 1×SSC at 55° C. Most preferably the hybridization is conducted under high stringency conditions which include hybridization in 50% formamide, 1 M NaCl, 1% SDS at 37° C., and a wash in 0.1×SSC at 60° C.

An extensive guide to the hybridization of nucleic acids is found in Tijssen, *Laboratory Techniques in Biochemistry and Molecular Biology—Hybridization with Nucleic Acid Probes*, Part I, Chapter 2 *"Overview of principles of hybridization and the strategy of nucleic acid probe assays"*, Elsevier, N.Y. (1993); and *Current Protocols in Molecular Biology*, Chapter 2, Ausubel, et al., Eds., Greene Publishing and wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481–486 (1997).

In one aspect of the invention, nucleic acids can be amplified from a plant nucleic acid library. The nucleic acid library may be a cDNA library, a genomic library, or a library generally constructed from nuclear transcripts at any stage of intron processing. Libraries can be made from a variety of plant tissues.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence identity to the sequences of the invention. See, for example, Sambrook et al. (1989) *Molecular Cloning: A Laboratory Manual* (2d ed., Cold Spring Harbor Laboratory Press, Plainview, New York), and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al, *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:1859–1862 (1981); the solid phase phosphoramidite triester method described by Beaucage and Caruthers, *Tetra. Letts.* 22(20):1859–1862 (1981), e.g., using an automated synthesizer, e.g., as described in Needham-VanDevanter et al., *Nucleic Acids Res.*, 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Expression Cassettes

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of expression cassettes that can be employed in conjunction with the present invention is well known to those of skill in the art in light of the present disclosure. See, e.g., Sambrook, et al.; *Molecular Cloning: A Laboratory Manual*; Cold Spring Harbor, N.Y.; (1989); Gelvin, et al.; *Plant Molecular Biology Manual*; (1990); *Plant Biotechnology: Commercial Prospects and Problems*, eds. Prakash, et al.; Oxford & IBH Publishing Co.; New Delhi, India; (1993); and Heslot, et al.; *Molecular Biology and Genetic Engineering of Yeasts*; CRC Press, Inc., USA; (1992); each incorporated herein in its entirety by reference.

For example, plant expression vectors may include (1) a cloned plant nucleic acid under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

Examples of inducible promoters are the Adh1 promoter which is inducible by hypoxia or cold stress, the Hsp70 promoter which is inducible by heat stress, and the PPDK promoter which is inducible by light. Also useful are promoters which are chemically inducible.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promote, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47, 95–102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18 (21), 6426 (1990). See the following site relating to the waxy promoter: Kloesgen, R. B., Gierl, A., Schwarz-Sommer, Z S. and Saedler, H., Molecular analysis of the waxy locus of *Zea mays, Mol. Gen. Genet.* 203, 237–244 (1986). Promoters that express in the embryo, pericarp, and endosperm are disclosed in U.S. applications Ser. Nos. 60/097,233 filed Aug. 20, 1998 and 60/098,230 filed Aug. 28, 1998. The disclosures each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395–4405 (1988); Callis et al., *Genes Dev.* 1:1183–1200 (1987). Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic or herbicide resistance. Suitable genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of nucleic acids in higher plants are well known in the art and include vectors derived from the tumor-inducing (Ti) plasmid of *Agrobacterium tumefaciens* described by Rogers et al., Meth. In Enzymol. 153:253–277 (1987). Exemplary *A. tumefaciens* vectors useful herein are plasmids pKYLX6 and pKYLX7 of Schardl et al., Gene 61:1–11 (1987) and Berger et al., Proc. Natl. Acad. Sci. USA 86:8402–8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Nat'l. Acad. Sci. USA* 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

A method of down-regulation of the protein involves using PEST sequences that provide a target for degradation of the protein.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J. Am. Chem. Soc.* (1987) 109:1241–1243). Meyer, R. B., et al., *J. Am. Chem. Soc.* (1989) 111:8517–8519, effect covalent crosslinking to a target nucleotide using an alkylating agent complementary to the single-stranded target nucleotide sequence. A photo-activated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J. Am. Chem. Soc.* (1990) 112:2435–2437. Use of N4, N4-ethanocytosine as an alkylating agent to crosslink to single-stranded oligonucleotides has also been described by Webb and Matteucci, *J. Am. Chem. Soc.* (1986) 108:2764–2765; *Nucleic Acids Res.* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

Proteins of the present invention include proteins derived from the native protein by deletion (so-called truncation), addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the proteins of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

The isolated proteins of the present invention include a polypeptide comprising at least 23 contiguous amino acids encoded by any one of the nucleic acids of the present invention, or polypeptides which are conservatively modified variants thereof. The proteins of the present invention or variants thereof can comprise any number of contiguous amino acid residues from a polypeptide of the present invention, wherein that number is selected from the group of integers consisting of from 23 to the number of residues in a full-length polypeptide of the present invention. Optionally, this subsequence of contiguous amino acids is at least 25, 30, 35, or 40 amino acids in length, often at least 50, 60, 70, 80, or 90 amino acids in length.

The present invention includes catalytically active polypeptides (i.e., enzymes). Catalytically active polypeptides will generally have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

The present invention includes modifications that can be made to an inventive protein without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A protein of the present invention can be expressed in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the nucleic acid of interest can be isolated in significant quantities for introduction into the desired plant cells.

Host cells that can be used in the practice of this invention include prokaryotes, including bacterial hosts such as *Escherichia coli, Salmonella typhimurium*, and *Serratia marcescens*. Eukaryotic hosts such as yeast or filamentous fungi may also be used in this invention. It preferred to use plant promoters that do not cause expression of the polypeptide in bacteria.

Commonly used prokaryotic control sequences include promoters such as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using Bacillus sp. and Salmonella (Palva, et al., *Gene* 22:229–235 (1983); Mosbach, et al., *Nature* 302:543–545 (1983)).

Synthesis of heterologous proteins in yeast is well known. See Sherman, F., et al., *Methods in Yeast Genetics*, Cold Spring Harbor Laboratory (1 982). Two widely utilized yeast for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology*. Vol. 2: *Special Methods in Peptide Synthesis*, Part A.; Merrifield, et al., *J. Am. Chem. Soc.* 85:2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) is known to those of skill.

The proteins of this invention may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: N.Y. (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation of the polypeptides can be effected by increasing or decreasing the concentration and/or the composition of the polypeptides in a plant. The method comprises transforming a plant cell with an expression cassette comprising a polynucleotide of the present invention to obtain a transformed plant cell, growing the transformed plant cell under plant forming conditions, and expressing the polynucleotide in the plant for a time sufficient to modulate concentration and/or composition of the polypeptides in the plant or plant part.

In some embodiments, the content and/or composition of polypeptides of the present invention in a plant may be modulated by altering, in vivo or in vitro, the promoter of a non-isolated gene of the present invention to up-or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868.

In some embodiments, an isolated nucleic acid (e.g., a vector) comprising a promoter sequence is transfected into a plant cell. Subsequently, a plant cell comprising the isolated nucleic acid is selected for by means known to those of skill in the art such as, but not limited to, Southern blot, DNA sequencing, or PCR analysis using primers specific to the promoter and to the nucleic acid and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, concentration of the polypeptides is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development.

Modulating nucleic acid expression temporally and/or in particular tissues can be controlled by employing the appropriate promoter operably linked to a polynucleotide of the present invention in, for example, sense or antisense orientation as discussed in greater detail above. Induction of expression of a polynucleotide of the present invention can also be controlled by exogenous administration of an effective amount of inducing compound. Inducible promoters and inducing compounds that activate expression from these promoters are well known in the art.

In preferred embodiments, the polypeptides of the present invention are modulated in monocots or dicots, preferably corn, soybean, sunflower, sorghum, canola, wheat, alfalfa, cotton, rice, barley, millet, *Arabidopsis thaliana*, tomato, Brassica vegetables, peppers, potatoes, apples, spinach, or lettuce.

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988).

Typical methods for detecting proteins include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand (e.g., streptavidin) molecule that is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Methods of measuring enzyme kinetics are well known in the art. See, e.g., Segel, *Biochemical Calculations*, $2^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256: 495–497 (1975).

Other suitable techniques involve selection of libraries of recombinant antibodies in phage or similar vectors (see, e.g., Huse et al., *Science* 246:1275–1281 (1989); and Ward, et al., *Nature* 341:544–546 (1989); and Vaughan et al., *Nature Biotechnology*, 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14:845–851 (1996). Also, recombinant immunoglobulins may be produced. See, Cabilly, U.S. Pat. No. 4,816,567; and Queen et al., *Proc. Nat'l Acad. Sci.* 86:10029–10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transformation of Cells

The method of transformation/transfection is not critical to the invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide of the present invention, for example a cDNA, RNA or a genomic sequence, will be used to construct an expression cassette that can be introduced into the desired plant. Isolated nucleic acid acids of the present invention can be introduced into plants according techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet.* 22:421–477 (1988). For example, the DNA construct may be introduced directly into the genomic DNA of the plant cell using techniques such as electroporation, PEG-mediated transfection, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp.197–213 in Plant Cell, Tissue and Organ Culture, Fundamental Methods. eds. O. L. Gamborg and G. C. Phillips. Springer-Verlag Berlin Heidelberg N.Y., 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J.* 3:2717–2722 (1984). Electroporation techniques are described in Fromm et al., *Proc. Natl. Acad. Sci.* 82:5824 (1985). Ballistic transformation techniques are described in Klein et al., *Nature* 327:70–73 (1987).

*Agrobacterium tumefaciens*-meditated transformation techniques are well described in the scientific literature. See, for example Horsch et al., *Science* 233:496–498 (1984), and Fraley et al., *Proc. Natl. Acad. Sci.* 80:4803 (1983). For instance, Agrobacterium transformation of maize is described in. U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., *Plant Cell Physiol.* 25:1353, 1984), (3) the vortexing method (see, e.g., Kindle, *Proc. Natl. Acad. Sci. USA* 87:1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plane Mol. Biol. Reporter, 6:165 (1988). Expression of polypeptide coding nucleic acids can be obtained by injection of the DNA into reproductive organs of a plant as described by Pena et al., Nature 325:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., *The Plant Cell*, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by Agrobacterium can be achieved as described by Horsch et al., *Science*, 227:1229–1231 (1985) and Fraley et al., *Proc. Natl. Acad. Sci. USA* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants that can be used in the method of the invention include monocotyledonous and dicotyledonous plants. Preferred plants include corn, soybean, sunflower, sorghum, canola, wheat, alfalfa, cotton, rice, barley, millet, *Arabidopsis thaliana*, tomato, Brassica vegetables, peppers, potatoes, apples, spinach, or lettuce.

Seeds derived from plants regenerated from transformed plant cells, plant parts or plant tissues, or progeny derived from the regenerated transformed plants, may be used directly as feed or food, or further processing may occur.

The present invention will be further described by reference to the following detailed examples. It is understood, however, that there are many extensions, variations, and modifications on the basic theme of the present invention beyond that shown in the examples and description, which are within the spirit and scope of the present invention. All publications, patents, and patent applications cited herein are hereby incorporated by reference.

EXAMPLES
Identification of a Phytyl/prenyltransferase Involved in Biosynthesis of Tocopherols in Synechocystis PCC 6803 and *Arabidopsis thaliana*.

PCC 6803 was used as a tool for identification of genes encoding enzymes involved in biosynthesis of tocopherols. Synechocystis is a cyanobacterium capable of tocopherol biosynthesis. The entire genome of this photosynthetic organism has been recently sequenced (Kaneko et al., 1996) and the data is available on a public searchable database, called CyanoBase. Using CyanoBase, we have identified an open reading frame (SLR1736) encoding a phytyl/prenyltransferase involved in the biosynthesis of 2-methyl-6-phytylplastoquinol, one of the tocopherol precursors. This open reading frame was identfied based on similarity with the phytyl/prenyltransferase SLR0056, a phytyl/prenyltransferase involved in the biosynthesis of chlorophyll in Synechocystis PCC 6803. SLR0056 exhibits a high homology with the previously identified chlorophyllide/phytyl/prenyltransferases from many cyanobacteria and *A. thaliana* (Lopez et al., 1996), suggesting that this enzyme is also involved in chlorophyll synthesis.

SLR1736 is similar, but not highly homologous to the SLR0056 open reading frame. However, the putative prenyl-binding domain is highly conserved in SLR1736, making it a good candidate for the tocopherol phytyl/prenyltransferase. Using the SLR1736 translated sequence as a query in the blast search, a genomic clone on chromosome II was identified in the *A. thaliana* database (Stanford Genomic Resources). This genomic clone was used to isolate an Arabidopsis cDNA clone. The F19F24 genomic clone and Arabidopsis cDNA are highly homologous to the SLR1736 protein sequence. The prenyl-binding domain is also conserved in the F19F24 and Arabidopsis cDNA. In addition, the amino terminal deduced amino acid sequence of the Arabidopsis gene and cDNA exhibits the traits of chloroplast-targeting sequences. Tocopherol biosynthesis has been shown to take place in chloroplast envelopes (Soll et al., 1980; Soll, 1987). We believe that the Arabidopsis F19F24 gene and homologous cDNA represent the orthologous phytyl/prenyltransferase that attaches phytyldiphosphate (phytyl-PP) and/or geranylgeranyl pyrophosphate (GGPP) to homogentisic acid in tocopherol synthesis in *A. thaliana*. Additionally, a 1.2 kb corn EST, chste82, that is highly homologous to SLR1736 has been also identified in a blast search.

To demonstrate that SLR1736 might be involved in tocopherol biosynthesis in Synechocystis, this gene was disrupted by insertion of the kanamycin expression cassette. The method of gene disruption by gene replacement technique has been previously described (Williams, 1988). The resulting mutant was named ΔSLR1736. Before analyses, the mutant was sub-cultured at least 6 times by single colony section on kanamycin to select for the colonies containing only copies of the SLR1736 gene disrupted with the kanamycin resistance gene. The absence of wild type SLR1736 genes was confirmed by PCR. The lack of tocopherols in the mutant was shown by HPLC separation of lipid extracts from wild type and mutant Synechocystis on a normal-phase column using fluorescent detection (FLD). Levels of phylloquinone (vitamin K1) and plastoquinone seem to be unaffected in this mutant. This suggests that there are at least two separate prenyltransferase activities for tocopherol and plastoquinone synthesis in Synechocystis and we may be able to manipulate carbon flow through the pathway by altering gene expression of either. Phytylation/prenylation of homogentisic acid is the branch-point in tocopherol and plastoquinone synthesis, and therefore, most likely an important regulatory point of the pathway. As well as the prenylation activities, availability of different prenyl tails may also be crucial for the regulation of carbon flow through the pathway. This will become significant for manipulating tocopherol levels in higher plants.

Amplification of the SLR1736 Open Reading Frame from Synechocystis

Chromosomal DNA from wild type Synechocystis PCC 6803 was isolated according to Williams (Methods in Enzymology (1987) 167:766–778). The primers represented by SEQ ID NOS: 7 (SLR1736F) and 8 (SLR1736R) were designed using Mac Vector computer program to amplify a 1.022 kb fragment containing the SLR1736 open reading frame. NdeI and BamHI sites were added to the primers to facilitate sub-cloning for expression purposes. ATG in the SLR1736F primer is the start codon for the SLR1736 open reading frame published in the CyanoBase Web-site. Taq polymerase (Gibco BRL) was used for gene disruption purposes and later Vent polymerase (NEB) was used for expression purposes following the manufacturer's recommendations. The following cycles were performed:

For Taq polymerase amplification:

95° C./5 minutes (1 cycle)

95° C./45 seconds, 45° C./45 seconds, 68° C./45 seconds (5 cycles)

95° C./45 seconds, 52° C./45 seconds, 72° C./45 seconds (30 cycles)

72° C./10 minutes

The same thermocycler conditions were used to amplify SLR1736 with Vent polymerase except that elongation times were extended to 2 minutes.

Sub-cloning the SRL1736 PCR Product

Plasmid pBluescript KS II (Stratagene) was digested with EcoRV (NEB) according to manufacturer's protocols. Both linearized pBluescript and the amplified SLR1736 open reading frame were separated by 0.9% agarose TBE gel electrophoresis. The bands were excised and purified from the gel using a JetSorb DNA purification kit (PGC Scientifics). The purified fragment was sub-cloned into the EcoRV site of pBluescript KS II in a blunt-end ligation reaction. A 10 µl ligation reaction contained 20 mM Tris-HCl (pH 7.6), 5 mM MgCl$_2$, 5 mM DTT, 50 µl g/ml BSA, 0.5 mM rATP, 15% PEG, and 1 U of T4 DNA ligase (Gibco BRL). Ligation was carried out at room temperature for 4 hours. One half of the reaction mixture was used to transform competent *E. coli* DH5α cells. Transformants were then selected on LB plates containing 100 mg/L of ampicillin. X-gal and IPTG were used for blue/white selection. White ampicillin resistant colonies were then selected, grown in liquid LB/ampicillin media, and plasmids were purified. The resulting plasmid was designated as KS-1736 and the nature and the orientation of the 1736 insert was determined by restriction digestion and sequencing (ABI Prism 310 Genetic Analyser). Clone #5, in which SLR1736 was in a reverse orientation to the Lac promoter of the vector, was selected for further manipulations.

The SLR1736 Replacement Construct

Transformation followed by homologous recombination is feasible in Synechocystis (Williams, 1988). A gene of interest, in our case SLR1736, can be easily disrupted by inserting an antibiotic resistance gene into the coding region. Such a disruption construct can be transformed into Synechocystis. pBluescript KS or any other vector capable of replication in *E. coli* can be used as a vector. These vectors cannot be replicated by DNA replication machinery of Synechocystis so that the cells are forced to keep the resistance gene by other means when kept on the antibiotic selection. In Synechocystis, the wild type copies of the target gene are replaced with the copies of this gene disrupted with the antibiotic resistance cassette by homologous recombination. Since this cyanobacterium contains multiple copies of its genome, it is necessary to streak selected resistant colonies on the selection media several times. This should ensure replacement of the wild type copies of the gene with the disrupted ones (Williams, 1988).

The kanamycin resistance gene from the transposon Tn903 encoding aminoglycoside 3'-phosphotransferase was used to disrupt the wild type SLR1736 gene. Plasmid pUC4K (Pharmacia) was cut with EcoRI to release the kanamycin resistance expression cassette. Since SLR1736 has a unique MfeI site about 200 bp from the beginning of the gene, plasmid KS-1736 #5 was digested with MfeI (NEB). MfeI leaves 5'-cohesive ends compatible with EcoRI so that no other molecular manipulations are necessary. The two DNA fragments were purified from agarose gels as described above and ligated using T4 DNA ligase (Gibco BRL) as recommended by the manufacturer. Competent *E. coli* DH5α cells were transformed with the ligation reaction and transformants selected on LB plates containing 50 mg of kanamycin per liter of media. Plasmids were purified and subjected to restriction analysis. Two plasmids having opposite orientation of the kanamycin cassette were chosen for Synechocystis transformation. The two constructs were designated as KSΔ1736-KAN-F and B, respectively, to indicate the orientation of the kanamycin resistance gene in respect to the SLR1736 gene.

Transformation of Synechocystis PCC 6803 with KSΔ1736-KAN-F and B, respectively, was carried out as described by Williams (1988). Transformants were selected on BG-11 plates containing 15 mM glucose and 5 mg of kanamycin per liter of medium. Two independent colonies from each transformation were then sub-cultured once a week for several weeks on BG-11 plates containing 15 mM glucose and 15 mg/L kanamycin before being analyzed. The cells were grown under continuous light at 30° C. The resulting clones used for further analyses were designated ΔSLR1736 F-1, F-2, B-1, and B-2.

Confirmation of the SLR1736 Gene Disruption by PCR

Chromosomal DNA from wild type and ΔSLR1736 mutant Synechocystis PCC 6803 was isolated from a few colonies according to Cai and Wolk (1990) with minor modifications as follows: Cells were resuspended in 200 µl of 50 mM Tris.HCl and 10 mM EDTA solution of pH 7.5. The cells were then transferred to a 2 ml screw-cup tube. 10 µl of 20% SDS, 200 µl of phenol:chloroform (1:1), and white sand were added. The samples were mixed well by vortexing for 1 minute and then they were placed on ice for another minute. This step was repeated twice. The mixture was centrifuged at 14,000 rpm for 5 minutes to separate organic and aqueous layers. The top aqueous phase was then extracted twice with an equal volume of chloroform and precipitated with a quarter of volume of 3M potassium acetate (pH 4.8) and two volumes of 96% of ethanol. After an hour incubation at −20° C. and a ten-minute centrifugation at 14,000 rpm, genomic DNA was washed once with 80% of ethanol, dried in a speedvac for 2–3 minutes, and resuspended in 20 µl of water. DNA was diluted 1:10 with water and used as a template in PCR reactions. PCR was performed as described above using Taq polymerase (Gibco BRL). Insertion of the kanamycin cassette into the SLR1736 open reading frame was clearly demonstrated.

HPLC Analyses of the Lipid Extracts from Wild Type and Mutant Synechocystis.

Tocopherol Analysis

About 30 mg of wild type and ΔSLR1736 F and B mutant cells grown on solid plates as described above were harvested and resuspended in 450 µl of methanol: chloroform (2:1) containing 1 mg/ml of butylated hydroxytoluene (BHT) to prevent oxidation of tocopherols. 200 ng of tocol was added as an internal standard. The cells were homogenized using mini-pestals followed by addition of 150 µl of chloroform and 300 µl of water to the mixture. After centrifugation (5 minutes at 14,000 rpm), the lower organic phase was transferred to a clean microfuge tube and dried in a speedvac. Lipids were resuspended in 80 µl of hexane containing 1 mg/ml of BHT. 40 µl of the lipid extract was subjected to HPLC (Hewlett-Packard 1100 Series HPLC system with a fluorescence detector) using a normal phase column (Lichrosorb Si60A 4.6×250 mm) equilibrated at 42° C. A 20-minute linear gradient of 8% to 18% di-isopropyl ether in hexane was used to separate different types of tocopherols. After excitation at a wavelength of 290 nm, tocopherols were detected by their fluorescence at 325 nm.

Wild type Synechocystis accumulates predominantly α-tocopherol. The ΔSLR1736 disruption mutants lack all tocopherols and this effect is independent of the kanamycin cassette orientation. These results indicate that SLR1736 is involved in tocopherol biosynthesis and acts upstream of the methyltransferases. Disruption of the methyltransferase genes SLL0418 (2-methyl-6-phytylplastoquinol methyltransferase) and SLR0089 (γ-tocopherol methyltransferase) which have been recently cloned from Synechocystis leads to the accumulation of β- and γ-tocopherols, respectively (Shintani, D., personal communication; Shintani and DellaPenna, 1998). The only two possible remaining enzymes are the cyclase and prenyltransferase. Since SLR1736 exhibits a similarity to known prenyltransferases, we believe this enzyme represents a prenyltransferase. More conclusive proof than the one based on similarity would be given by in vitro prenyltransferase assays and feeding studies of wild type and ΔSLR1736 mutant Synechocystis with $^{14}$C uniformly labeled tyrosine.

Phylloquinone and Plastoquinone Analysis

Formation of homogentisic acid, the first step of the pathway, is common for both tocopherols and plastoquinone in photosynthetic organisms. To answer the question if the tocopherol prenyltransferase is also involved in plastoquinone biosynthesis and how carbon flow is affected in the plastoquinone part of the pathway, we analyzed lipid extracts from wild type and the mutant cells. On the other hand, the phytyl tail is a part of vitamin K1 (phylloquinone) molecule. To estimate effects of the SLR1736 gene disruption on the phylloquinone biosynthesis in Synechocystis, we also performed vitamin K1 analysis.

About 30 mg of wild type and ΔSLR1736 F and B mutant were harvested and resuspended in 450 µl of methanol:chloroform (2:1). The cells were homogenized using mini-pestals followed by addition of 150 µl of chloroform and 300 µl of water to the mixture. After centrifugation (5 minutes at 14,000 rpm), the lower organic phase was transferred to a clean microfuge tube, dried in a speedvac, dissolved in 30 µl of ethyl acetate, and oxidized with silver oxide for a half an hour. The entire extract was loaded on a TLC plate (Silica, 60A) which was developed in 20% diethyl ether in petroleum ether and dried. The plate was sprayed with leucomethylene blue (Crane & Barr, 1971) to visualize any changes in quinone composition. No differences between the wild type and mutant quinone profiles were observed. To prepare leucomethylene blue, 50 mg of methylene blue and 0.5 g of zinc dust were mixed in 5 ml of water. The mixture was acidified with a few drops of concentrated sulfuric acid and left to react for about 10 minutes before use.

To quantify possible changes in quinone content in wild type and mutant Synechocystis, HPLC analyses of lipid extracts containing plastoquinone-8 as an internal standard were performed. Lipids were extracted as described above except that 1 µg of plastoquinone-8 was added in the beginning of extraction. Plastoquinone-8 and plastoquinone-9 standards were isolated and purified from Iris holandica bulbs (Hutson & Therfall, 1980) and their concentrations were determined using the molar absorption coefficient of plastoquinone-9 at 254 nm, 17.94 mM$^{-1}$ cm$^{-1}$. These quinones have similar properties and they can be easily separated by the HPLC method described below. Therefore, plastoquinone-8 is an excellent internal standard.

After extraction, quinones were resuspended in 80 µl of HPLC grade ethyl acetate. 40 µl of the lipid extract was subjected to HPLC (Hewlett-Packard 1100 Series HPLC system) using a C-18 reverse phase column (Spherisorb, 4.6×250 mm). The following conditions were utilized to separate different quinones:

| Time (min.): | Reagent Alcohol (%): | Water (%): |
| --- | --- | --- |
| 0 | 90 | 10 |
| 1 | 99 | 1 |
| 10 | 99 | 1 |
| 11 | 100 | 0 |
| 16 | 100 | 0 |
| 17 | 90 | 10 |
| 35 | 90 | 10 |

The flow of the solvents was 0.8 ml/min and the separation was performed at room temperature. Quinones were detected by their absorbance at 250 and 275 nm using a diode array detector and the identity of phylloquinone and plastoquinone-9 was confirmed by comparison with their previously published spectra (Crane & Barr, 1971). No differences in vitamin K1 and plastoquinone-9 compositions were observed between wild type and the ΔSLR1736 disruption mutant. This indicates that the SLR1736 gene product is involved only in tocopherol biosynthesis.

Cloning Phytyl Transferase from A. thaliana Involved in Tocopherol Biosynehesis

A developing seed-specific cDNA library from A.thaliana (lambda-ZAP type, provided by John Ohirogge at the Michigan State University) was screened using a PCR product from wild type A. thaliana genomic DNA (Ler ecotype) which exhibits a high degree of homology with the Synechocystis phytyl transferase. Primers represented by SEQ ID NO: 5 (AT1736F) and SEQ ID NO: 6 (AT1736B) were used to amplify about 1 kb fragment corresponding to 60238–61229 bp region of the BAC clone F19F24 (A. thaliana database at Stanford). The following program was used to amplify this fragment with Vent DNA polymerase (New England Biolabs):

95° C./5 minutes (1 cycle)

95° C./45 seconds; 50° C./45 seconds, 72° C./1 minute (30 cycles)

72° C./10 minutes (1 cycle).

The PCR product was then sub-cloned into EcoRV site of pBluescript KS (Stratagene) as in the case of the cyanobacterial phytyl transferase presented above and sequenced from both ends using T3 and T7 primers (Stratagene) to ensure the identity of the sub-cloned fragment. A 300 bp fragment of the insert (5'-end) was released with EcoRI from the vector and used as a radioactively-labeled probe to obtain full-length clones. About 2.5 million plaques of the seed-specific library were screened using standard procedures (Sambrook, J., Fritsch, E. F. & Maniatis, T. (1989). Molecular Cloning. 2$^{nd}$ edition, Cold Spring Harbor Laboratory Press). 16 positive non-purified plaques were chosen for PCR analysis using T3 and SEQ ID NO: 30 (AT1736T7c) which is an internal primer for the phytyl transferase. Clones #1, 3, 5, 8, 11, 12, and 14 were selected for further purification and single clone excision, performed according to manufacturer (Stratagene), to obtain individual clones in pBluescript SK plasmids. Each clone was sequenced from each end using T3 and T7 primer. The longest clone, #11—about 1.6 kb, was chosen for complete sequencing which is in progress now. All clones were aligned to the genomic clone F19F24 from *A. thaliana* to confirm their identity, identify introns and find possible sequencing mistakes in the genomic sequence. We believe that ATG codon (59220 bp on F19F24) is the start codon of the phytyl transferase involved in tocopherol synthesis in *A. thaliana*. Starting from this methionine, the first 36 amino acids represent the chloroplast thylakoid membrane-targeting sequence.

Confirmation of Prenyltransferase Nature of SLR1736

To confirm the prenyltransferase nature of SLR1736, the intact gene will be expressed in *E. coli* because this bacterium lacks any enzymatic activity connected to tocopherol biosynthesis. Therefore, SLR1736 activity will be shown by an in vitro phytyl/prenyltransferase assay using protein extracts from *E. coli* expressing SLR1736 or by reconstruction of multiple steps of the pathway in *E. coli* $^{14}$C uniformly labeled p-hydroxyphenyl pyruvate and phytyl-PP, or other prenyl diphosphates will be used as substrates. p-hydroxyphenyl pyruvate dioxygenase catalyses conversion of p-hydroxyphenylpyruvic acid to homogentisic acid, the immediate substrate for the tocopherol and plastoquinone prenyltransferase(s). Therefore, *A. thaliana* p-hydroxyphenylpyruvic acid dioxygenase (Norris et al., 1998) expressed in *E. coli* along with the prenyltransferase will be present in the reactions to couple the two enzymatic steps. To further show that SLR1736 is a prenyltransferase, ΔSLR1736 and wild type Synechocystis will be grown in the presence of $^{14}$C uniformly labeled L-tyrosine to trace prenylated products by using TLC and autoradiography.

The SLR1736 open reading frame will be also expressed in *E. coli* in the presence of p-hydroxyphenylpyruvic acid dioxygenase (Norris et al., 1998), *Adonis paleastina* geranylgeranyl diphosphate synthase (gift from F. Cunningham), and geranylgeranyl hydrogenase from Synechocystis (SLL1091, Addlesee et al., 1996; Keller et al., 1998) to reconstitute the phytyl pyrophosphate pathway since *E. coli* does not possess any of these enzymatic activities. Lipids will be extracted and subjected to HPLC analysis of quinones as described above. 2-methyl-6-phytylplastoquinone is stable and should be present in *E. coli* lipid extracts.

SLR1736 Homologue from *A. thaliana* (AT1736)

To investigate the role of the plant homologue of SLR1736, the intact full length cDNA from *Arabidopsis thaliana* (AT1736) and corn chste82 EST will be expressed in the sense and antisense orientation from the constitutive CaMV 35S or seed-specific (Seffens et al., 1990) promoters, respectively, in *A. thaliana*. Visible phenotype(s) will be observed and lipids from the transgenic plants will be extracted and subjected to HPLC/FLD analyses to detect changes in tocopherol content and composition in green tissues and seeds. Plastoquinone and phyloquinone levels will also be analyzed as described above. It is possible that phytyl-PP is limiting for the prenyltransferase activity. Consequently, we may want to overexpress geranylgeranyl pyrophosphate synthase and GGDP dehydrogenase to elevate phytl-PP levels in *A. thaliana*. Columbia ecotype Arabidopsis plants will be transformed with these overexpression constructs separately and homozygous transformants will be crossed to obtain plants containing all three constructs.

The in vitro prenyltransferase assay will be performed with AT1736 expressed in *E. coli* as described above for SLR1736. Prenyl tail-specificity studies will be also carried out with this enzyme, using various tails such as GGDP, phytyl-PP, and solanyl-PP. As in the case of SLR1736 from Synechocystis, it is important to determine if there are one or two prenyltransferases for tocopherol and plastoquinone biosynthesis in higher plants.

Construction of p0018 Maize cDNA Libraries

Total RNA Isolation

Total RNA was isolated from p0018 library corn tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. Anal. Biochem. 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation

The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to para-magnetic particles and a magnetic separation stand. The mRNA was washed at high stringent condition and eluted by RNase-free deionized water.

cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-32P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

Sequencing of Maize cDNA and Library Subtraction

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure are plated out on 22×22 cm2 agar plate at density of about 3,000 colonies per plate. The plates are incubated in a 37° C. incubator for 12–24 hours. Colonies are picked into 384-well plates by a robot colony picker, Q-bot (GENETIX Limited). These plates are incubated overnight at 37° C.

Once sufficient colonies are picked, they were pinned onto 22×22 cm2 nylon membranes using Q-bot. Each membrane contained 9,216 colonies or 36,864 colonies. These membranes are placed onto agar plate with appropriate antibiotic. The plates are incubated at 37° C. for overnight.

After colonies are recovered on the second day, these filters are placed on filter paper prewetted with denaturing solution for four minutes, then are incubated on top of a boiling water bath for additional four minutes. The filters are then placed on filter paper prewetted with neutralizing solution for four minutes. After excess solution is removed by placing the filters on dry filter papers for one minute, the colony side of the filters are place into Proteinase K solution, incubated at 37° C. for 40–50 minutes. The filters are placed on dry filter papers to dry overnight. DNA is then cross-linked to nylon membrane by UV light treatment.

Colony hybridization is conducted as described by Sambrook, J., Fritsch, E. F. and Maniatis, T., (in Molecular Cloning: A laboratory Manual, 2nd Edition). The following probes were used in colony hybridization:

Construction of Additional Maize, Rice, Soybean and Wheat cDNA Libraries

Composition of cDNA Libraries; Isolation and Sequencing of cDNA Clones cDNA libraries representing mRNAs from maize, rice, soybean and wheat tissues were prepared. The characteristics of these libraries are described in Table 1.

TABLE 1

| Library Designation | Library Description | Clone |
| --- | --- | --- |
| cco1n | Corn Cob of 67 Day Old Plants Grown in Green House* | cco1n.pk087.117 |
| p0018 | Seedling after 10 day drought (T001), heat shocked for 24 hrs (T002), recovery at normal growth condition for 8 hrs, 16 hrs, 24 hrs | p0018.chste82r:fis |
| p0108 | PR leaves + C. carbonium, screened 1 Pool of PR + C. carbonium tox-3h; PR + C. carbonium tox-6h; PR + C. carbonium tox-24h; PR + C. carbonium tox-48hr; and PR + C. carbonium tox-77 days | p0108.cjrmc89r:fis |
| rca1n | Rice )Oryza sativa L., Nipponbare) callus normalized. | rca1n.pk025.c4 |
| r10n | Rice 15 Day Old Leaf* | r10n.pk0066.e2:fis |
| scr1c | Soybean (Glycine max L., 2872) Embryogenic suspension culture subjected to 4 vacuum cycles and collected 12 hrs later (control scb1c). | scr1c.pk005.12 |
| sgc7c | Soybean (Glycine max L., Wye) germanating cotyledon (yellow and wilting; 18–30 DAG). | sgc7c.pk001.h22 |
| src2c | Soybean (Glycine max L., 437654) 8 day old root inoculated with eggs of cyst Nematode (Race 1) for 4 days. | src2c.pk020,d5:fis |
| wdk2c | Wheat Developing Kernel, 7 Days After Anthesis. | wdk2c.pk012.f2 |
| wlm0 | Wheat Seedlings 0 Hour After Inoculation with *Erysiphe graminis f. sp tritici* | wlm0.pk0011.c7 |

*These libraries were normalized essentially as described in U.S. Pat. No. 5,482,845, incorporated herein by reference.

1. First strand cDNA from the same tissue as the library was made to remove the most redundant clones.
2. 48–192 most redundant cDNA clones from the same library based on previous sequencing data.
3. 192 most redundant cDNA clones in the entire corn sequence database.
4. A Sal-A20 oligo nucleotide removes clones containing a poly A tail but no cDNA.
5. cDNA clones derived from rRNA.

The image of the autoradiography is scanned into computer and the signal intensity and cold colony addresses of each colony is analyzed. Re-arraying of cold-colonies from 384 well plates to 96 well plates is conducted using Q-bot.

Identification of Gene from a Computer Homology Search

Gene identities were determined by conducting BLAST (Basic Local Alignment Search Tool; Altschul, S. F., et al., (1993) *J. Mol. Biol.* 215:403–410; searches under default parameters for similarity to sequences contained in the BLAST "nr" database (comprising all non-redundant Gen-Bank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. In some cases, the sequencing data from two or more clones containing overlapping segments of DNA were used to construct contiguous DNA sequences.

In general, cDNA libraries may be prepared by the method described above or by any one of many other methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Characterization of cDNA Clones Encoding Phytyl/prenyltransferase.

cDNA Clones were identified by computer homology search as described above. The BLASTP and BLASTN searches using the sequences from clones listed in Table 1 revealed similarity to certain polypeptides as shown in Table 2. The "/blast/data/2.0/2/nr" database was searched. GAP results showing % identity to synechocystis and arabidopsis are also shown. Table 2 shows the BLAST results for individual complete gene sequences ("CGS").

TABLE 2

Top BLAST Results for Sequences Encoding Polypeptides Homologous
to Phytyl/prenyltransferase and GAP % Identity to Synechocystis and Arabidopsis

| Clone | Status | Protein Sequence with Significant Alignment gi# (accession #) Organism; % Blast Identity | GAP % Identity Clone to D90909 | GAP % Identity Clone to AC003673 |
|---|---|---|---|---|
| SEQ ID 12 - Contig of: cco1n.pk087.117 and cen3n.pk0012.h6 | CGS | 1652856 (D90909) Synechocystis; 36% 3004556 (AC003673) Arabidopsis; 32% | 36.80% | 50.27% |
| SEQ ID 4 - p0018.chste82r:fis | CGS | 1652856 (D90909) Synechocystis; 43% 3004556 (AC003673) Arabidopsis; 47% | 43.58% | 70.67% |
| SEQ ID 14 - p0108.cjrmc89r:fis | CGS | 1652856 (D90909) Synechocystis; 36% 6015890 (Y18930) Sulfolobus; 30% 5103549 (AP000058) Aeropyrum; 32% 3004556 (AC003673) Arabidopsis; 26% | 37.54% | 30.30% |
| SEQ ID 16 - rca1n.pk025.c4 | CGS | 1652856 (D90909) Synechocystis; 45% 3004556 (AC003673) Arabidopsis; 43% | 45.27% | 70.67% |
| SEQ ID 18 - r10n.pk0066.e2:fis | CGS | 1652856 (D90909) Synechocystis; 35% 5103549 (AP000058) Aeropyrum; 29% 6015890 (Y18930) Sulfolobus; 28% 3004556 (AC003673) Arabidopsis; 25% | 35.59% | 31.16% |
| SEQ ID 20 - scr1c.pk005.12 | CGS | 1652856 (D90909) Synechocystis; 37% 6015890 (Y18930) Sulfolobus; 28% 3004556 (AC003673) Arabidopsis; 25% | 36.95% | 33.33% |
| SEQ ID 22 - Contig of: sgc7c.pk001.h22 | CGS | 1652856 (D90909) Synochocystis; 44% 3004556 (AC003673) Arabidopsis; 83% | 44.90% | 75.48% |
| SEQ ID 24 - src2c.pk020.d5:fis | CGS | 3004556 (AC003673) Arabidopsis; 39% 1652856 (D90909) Synechocystis; 29% | 30.51% | 52.62% |
| SEQ ID 26 - Contig of: wdk2c.pk012.f2 | Partial Gene Seq | 3004556 (AC003673) Arabidopsis; 45% 1652856 (D90909) Synechocystis; 37% | 37.50% | 43.75% |
| SEQ ID 28 - Contig of: wlm0.pk0011.c7 | CGS | 1652856 (D90909) Synechocystis; 36% 3004556 (AC003673) Arabidopsis; 27% | 37.54% | 30.30% |

Sequence alignments and BLAST sequence identities indicate that the nucleic acid fragments comprising the instant cDNA clones encode a substantial portion of a phytyl/prenyltransferase.

A BLASTN search of "/blast/data/2.0/3/est" using the sequences from clones listed in Table 1 showed homology (E score>140) to the following sequences on Table 3 as indicated by Genbank Accession number.

TABLE 3

GAP Search Result

| Number | Species | Shows Homology With Seq ID No |
|---|---|---|
| C25006 | Rice | 17 |
| C74444 | Rice | 15 |
| AA750728 | Rice | 15 |
| M749638 | Rice | 15 |
| AU029707 | Rice | 15 |
| AI612332 | Corn | 13 |
| AI711952 | Corn | 13 |
| AI795680 | Corn | 13 |
| AI897027 | Tomato | 21 |
| AI938270 | Soybean | 21 |
| AI938569 | Soybean | 21 |
|  |  | 23 |
| AI948381 | Corn | 13 |
| AW052841 | Corn | 13 |
| AW054141 | Corn | 11 |
| AW066179 | Corn | 11 |
| AW146615 | Corn | 13, 17 |
| AW202246 | Soybean | 19 |
| AI444024 | Soybean | 19 |
| AI442111 | Soybean | 19 |
| AW132909 | Soybean | 23 |
|  |  | 21 |
| AI748688 | Soybean | 21 |
| AI939002 | Soybean | 19 |
| AW306617 | Soybean | 21 |
| AW433064 | Soybean | 21 |
| AW563431 | Sorghum | 17 |

In sequencing clone containing SEQ ID NO: 11, an extra nucleotide at nt 631 was observed. In addition, possible frameshifts at nt 107–140 were located that may interrupt homology to the Synechocystis hypothetical protein #1652856. The extra nucleotide at nt 631 was deleted from the sequence listing provided with this application, and sequence identity was determined without considering the extra nucleotide. The extra nucleotide is likely an artifact occurring during the isolation and sequencing of the cDNA clones.

Clones p0108.cjrmc89r:fis and r10n.pk0066.e2:fis each contain substantially complete gene sequence, with the exception of a few N-terminal amino acids on each.

Clone wdk2c.pk012.f2 has an apparent intron from nt 322 to 426, as determined by GT/AG intron borders, that interrupt homology to p0018.chste82r:fis. The sequence listing provides both the nucleotide sequence of the clone with the intron (SEQ ID NO: 29) and without the intron (SEQ ID NO: 25). Amino acid sequence identity in SEQ ID NO: 26 was determined after removal of the intron.

The amino acid sequence of clone wlm0.pk0011.c7 covers the entire phytyl/prenyltransferase and contains a putative transit peptide sequence.

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the BudapestTreaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al. (1987) Nature 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al. (1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. this fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supematant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Expression of Maize Phytyl/prenyltransferase in Soybean Somatic Embryos

The ability to change the levels of total tocopherol levels in plants by transforming them with sequences encoding the maize phytyl/prenyltransferase was tested by preparing transgenic soybean somatic embryos and assaying the tocopherol and oil levels. Plasmid DNA from clone poo18chste82r was used as a template for the amplification of the open reading from pcr by using the primers represented by SEQ ID NO: 31 (forward primer) and SEQ ID NO: 32 (reverse primer). Pfu polymerase was used according to the manufacturers recommendations (Stratagene). The following pcr reaction mix contained the following: 5 ng plasmid, 25 nmoles dNTPs, 5% DMSO, 1×pcr buffer (supplied), 30 nmoles primers, 5U pfu polymerase in 100 ul reaction volume. The pcr reaction conditions were as follows Step 1, 45 s 94° C.; step 2 25 cycles of 45 s 94° C., 45 s 58° C. annealing, 2 min extension 72° C. Step 3 72° C. 10 min, step 4 0° C. The pcr product was purified by agarose gel electrophoresis (!% agarose in TAE), the ethidium bromide visualized band cut out and purified from the gel by using a QIAquick Gel Extraction kit (Qiagen) according to the manufacturers recommendations. The purified pcr product (200 ng) was ligated into the srf I site of the plasmid PCR-Script cloning vector and the resultant plasmid was used to transform $E.coli$ DH10 cells. Colonies containing the 1.2 kb NotI fragment were identified by antibiotic (ampicillin selection) and blue/white (IPTG+X-gal) selection of colonies on LB/Amp plates. White (recombinant) colonies were picked and grown overnight on liquid LB/Amp culture. Positive clones were identified by plasmid preparation and restriction digest analysis for the presence of the 1.2 kB NotI fragment. Positive clones were used as template to fully sequence the phytyl transferase of (both strands). Plasmids containing the correct insert verified by nucleic acid sequence were digested with NotI and the 1.2 kb fragment ligated to NotI-digested and phosphatase-treated pKS67. The plasmid pKS67 was prepared by replacing in pRB20 (described in U.S. Pat. No. 5,846,784) the 800 bp Nos 3' fragment, with the 285 bp Nos 3' fragment containing the polyadenylation signal sequence and described in Depicker et al. (1982) *J. Mol. Appl. Genet.* 1:561–573. Clones were screened for the sense and antisense orientation of the phytyvprenyltransferase insert fragment by restriction enzyme digestion.

Transformation of Soybean Somatic Embryo Cultures

The stock solutions and media shown in Table 4 were used for transformation and propagation of soybean somatic embryos:

TABLE 4

Stock Solution and Media

| Stock Solutions | |
|---|---|
| | (g/L) |
| MS Sulfate 100x stock | |
| $MgSO_4.7H_2O$ | 37.0 |
| $MnSO_4.H_2O$ | 1.69 |
| $ZnSO_4.7H_2O$ | 0.86 |
| $CuSO_4.5H_2O$ | 0.0025 |
| MS Halides 100x stock | |
| $CaCl_2.2H_2O$ | 44.0 |
| KI | 0.083 |
| $CoCl_2.6H_2O$ | 0.00125 |

TABLE 4-continued

Stock Solution and Media

| | |
|---|---|
| $KH_2PO_4$ | 17.0 |
| $H_3BO_3$ | 0.62 |
| $Na_2MoO_4.2H_2O$ | 0.025 |
| $Na_2EDTA$ | 3.724 |
| $FeSO_4.7H_2O$ | 2.784 |
| B5 Vitamin stock | |
| myo-inositol | 100.0 |
| nicotinic acid | 1.0 |
| pyridoxine HCl | 1.0 |
| thiamine | 10.0 |
| Media | |
| SB55 (per Liter) | |
| 10 mL of each MS stock | |
| 1 mL of B5 Vitamin stock | |
| 0.8 g $NH_4NO_3$ | |
| 3.033 g $KNO_3$ | |
| 1 mL 2,4-D (10 mg/mL stock) | |
| 0.667 g asparagine | |
| pH 5.7 | |
| SB103 (per Liter) | |
| 1 pk. Murashige & Skoog salt mixture* | |
| 60 g maltose | |
| 2 g gelrite | |
| pH 5.7 | |
| SB148 (per Liter) | |
| 1 pk. Murashige & Skoog salt mixture* | |
| 60 g maltose | |
| 1 mL B5 vitamin stock | |
| 7 g agarose | |
| pH 5.7 | |

*(Gibco BRL)

Soybean embryonic suspension cultures were maintained in 35 mL liquid media (SB55) on a rotary shaker (150 rpm) at 28° C. with a mix of fluorescent and incandescent lights providing a 16 h day 8 h night cycle. Cultures were subcultured every 2 to 3 weeks by inoculating approximately 35 mg of tissue into 35 mL of fresh liquid media.

Soybean embryonic suspension cultures were transformed with the plasmid containing the phytyl/prenyltransferase sequence (positive orientation) by the method of particle gun bombardment (see Klein et al. (1987) *Nature* 327:70–73) using a DuPont Biolistic PDS1000/He instrument. Five µL of pKS94s plasmid DNA (1 g/L), 50 µL $CaCl_2$ (2.5 M), and 20 µL spermidine (0.1 M) were added to 50 µL of a 60 mg/mL 1 mm gold particle suspension. The particle preparation was agitated for 3 minutes, spun on a microfuge for 10 seconds and the supernate removed. The DNA-coated particles were then washed once with 400 µL of 70% ethanol and resuspended in 40 µL of anhydrous ethanol. The DNA/particle suspension was sonicated three times for 1 second each. Five µL of the DNA-coated gold particles were then loaded on each macro carrier disk.

Approximately 300 to 400 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded, and following bombardment, the tissue was divided in half, placed back into liquid media, and cultured as described above.

Fifteen days after bombardment, the liquid media was exchanged with fresh SB55 containing 50 mg/mL hygromycin. The selective media was refreshed weekly. Six weeks after bombardment, green, transformed tissue was isolated and inoculated into flasks to generate new transformed embryonic suspension cultures.

Transformed embryonic clusters were removed from liquid culture media and placed on a solid agar media, SB103, containing 0.5% charcoal to begin maturation. After 1 week, embryos were transferred to SB103 media minus charcoal. After 5 weeks on SB103 media, maturing embryos were separated and placed onto SB148 media. During maturation embryos were kept at 26° C. with a mix of fluorescent and incandescent lights providing a 16 h day 8 h night cycle. After 3 weeks on SB148 media, embryos were analyzed for the expression of the tocopherols. Each embryonic cluster gave rise to 5 to 20 somatic embryos.

Non-transformed somatic embryos were cultured by the same method as used for the transformed somatic embryos.

Analysis of Transformed Somatic Embryos

At the end of 3 weeks on SB148 medium somatic embryos were harvested from 33 independently transformed lines. Pools of five embryos/event were pooled, the fresh weight noted, the embryos frozen on dry ice and lyophilized overnight. The corresponding dry weight was noted, the embryos pulverized with a glass rod and tocopherols and oil extracted by the addition of 0.5 ml heptane (18 h, room temperature, dark). The embryos were re-extracted with 0.25 ml of heptane the solutions pooled and centrifuged (5 min, 12000 g). The supernatant was stored in amber hplc autosampler vials at −20° C. prior to analysis.

HPLC analysis of the extracts was carried out using an HP1100 system (Agilent Technologies). 25 ul of the heptane sample was applied to a Lichrosphere Si 60 column (5 micron 4×12.5 mm). The column was eluted with heptane/isopropanol (98:2 v/v) at a flow rate of 1 ml/min. After 6 minutes all four tocopherol isomers were eluted, as detected by a HPI 100 fluorescence detector (excitation wavelength 295 nm, emission wavelength 330 nm). Individual tocopherol standards (Matreya) were diluted with HPLC grade heptane to levels between 1 and 200 ng/ul to construct a six point external standard curve. Tocopherols in each sample were quantified using a standard curve run on the same day as the samples.

Total oil content of the samples was estimated by quantitative gas chromatography of the fatty acid methyl esters. 50 ul samples were derivitized by addition to 0.5 ml of a 1% (v/v) solution of sodium methoxide in methanol, 1 ug of undecanoic acid (17:0) dissolved in toluene was added as an internal standard. Derivitized fatty acids were extracted in 400 ul heptane, fatty acids separated by glc and the peak heights quantitated by using a HP 6890 gas liquid chromatograph equipped with a fused silica capillary column 30 m×i.d. 0.25 mm coated with polar phase Omegawax 320 (Supelco In, Bellfonte, Pa.), autosampler, flame ionization detector and ChemStation software on a HP The example shown in Table 5 shows the data from 33 independent transformed lines of somatic soy embryos (five pooled embryos per line) transformed with KS67 containing the maize phytyl/prenyltransferase in the positive orientation. Normal ratios of tocopherol (ngT)/oil (ugoil) in somatic embryos are 2–5. Overexpression of the phytyl/prenyltransferase has increased the amount of tocopherol relative to oil. In particular in samples 16 and 17 the ng/ugOil ratios have doubled to be 10.9 and 10.1 respectively.

TABLE 5

Lines Transformed with KS67 in Positive Orientation

| Sample | Oil (mg) | Tocopherol (ng) | ngT/ugOil |
|---|---|---|---|
| 1 | 313.2 | 1.25 | 3.98 |
| 2 | 162.5 | 0.51 | 3.2 |
| 3 | 195.9 | 1.29 | 6.6 |
| 4 | 133.7 | 0.69 | 5.2 |
| 5 | 323.5 | 0.95 | 2.9 |
| 6 | 18.6 | 0.13 | 7.1 |
| 7 | 121.3 | 0.32 | 2.6 |
| 8 | 98.9 | 0.73 | 7.4 |
| 9 | 175.2 | 0.5 | 2.8 |
| 10 | 314.5 | 1.3 | 4.1 |
| 11 | 99.4. | 0.5 | 5.1 |
| 12 | 75.1 | 0.23 | 3 |
| 13 | 105.9 | 0.59 | 5.5 |
| 14 | 381.2 | 1.15 | 3 |
| 15 | 248.1 | 1.44 | 5.8 |
| 16 | 103.8 | 1.13 | 10.9 |
| 17 | 165 | 1.67 | 10.1 |
| 18 | 117.3 | 0.5 | 4.3 |
| 19 | 255.7 | 0.77 | 3 |
| 20 | 365.1 | 1.8 | 4.9 |
| 21 | 253.9 | 0.79 | 3.1 |
| 22 | 88.7 | 0.59 | 6.6 |
| 23 | 454.2 | 1.23 | 2.7 |
| 24 | 352.5 | 1.61 | 4.6 |
| 25 | 240.9 | 0.63 | 2.6 |
| 26 | 404.2 | 2.19 | 5.4 |
| 27 | 323 | 1.52 | 4.7 |
| 28 | 386.2 | 2.28 | 5.9 |
| 29 | 253.5 | 1.28 | 5 |
| 30 | 211.9 | 1.35 | 6.4 |
| 31 | 460.5 | 1.3 | 2.8 |
| 32 | 161.7 | 1.19 | 7.3 |
| 33 | 275.5 | 1.66 | 6 |

TABLE 6

Detailed Analysis of each of the Five Embryos in Transformed Lines 15 (control), 16, 17 and 18 (control).

| Sample | Oil (mg) | Tocopherol (ng) | ngT/ugOil |
|---|---|---|---|
| SC515-1 | 1.36 | 10.6 | 7.8 |
| SC515-2 | 0.75 | 7.2 | 9.7 |
| SC515-3 | 0.93 | 5.4 | 5.8 |
| SC515-4 | 6.67 | 37.04 | 5.6 |
| SC515-5 | 1.35 | 10.1 | 7.5 |
| SC516-1 | 0.8 | 15.8 | 19.7 |
| SC516-2 | 0.4 | 10.7 | 26.8 |
| SC516-3 | 4.21 | 27.5 | 6.5 |
| SC516-4 | 0.2 | 3.5 | 17.5 |
| SC516-5 | 2.7 | 35.7 | 13.2 |
| SC517-1 | 0.4 | 44.3 | 111 |
| SC517-2 | 0.2 | 39.6 | 200 |
| SC517-3 | 5 | 58 | 11.7 |
| SC517-4 | 1.29 | 11.6 | 9 |
| SC517-5 | 24.7 | 197.8 | 13.5 |
| SC518-1 | 32.1 | 43.4 | 1.4 |
| SC518-2 | 31.6 | 6.1 | 1.9 |
| SC518-3 | 2.99 | 11.6 | 3.9 |
| SC518-4 | 0.7 | 6.1 | 8.7 |
| SC518-5 | 0.5 | 3.4 | 7 |

The single embryo analysis in Table 6 was conducted to confirm the pooled embryo data provided in Table 5. It should also be noted that an alternative embodiment of the invention involves somatic soy embryos transformed with KS67 containing the maize phytyvprenyltransferase in the reverse orientation.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

References

Addlesee, H. A., Gibson, L. C. D., Jensen, P. E. & Hunter, C. N. (1996). Cloning, sequencing and functional assignment of the chlorophyll biosynthesis gene, chlP, of Synechocystis sp. PCC 6803. FEBS Lett. 389: 126–130.

Cai, Y. & Wolk, C. P. (1990) Use of conditionally lethal gene in Anabena sp. strain PCC 7120 to select for double recombinants and to entrap insertion sequences. J. Bacteriol. 172:3138–3145.

Crane, F. L. & Barr, R. (1971). Determination of ubiquinones. Meth. Enzymol. 18:137–165.

Hutson, K. G. & Threlfall, D. R. (1980). Synthesis of plastoquinone-9 and phytylplastoquinone from homogentisate in lettuce chloroplasts. Biochim. Biophys. Acta 632:630–648.

Kaneko, T., Sato, S., Kotani, H., Tanaka, A., Asamizu, E., Nakamura, Y., Miyajima, N., Hirosawa, M., Sugiura, M., Sasamoto, S., Kimura, T., Hosouchi, T., Matsuno, A., Muraki, A., Nakazaki, N., Naruo, K., Okumura, S., Shimpo, S., Takeuchi, C., Wada, T., Watanabe, A., Yamada, M., Yasuda, M. & Tabata, S. (1996). Sequence analysis of the genome of the unicellular cyanobacterium Synechocystis sp. strain PCC6803. II. Sequence determination of the entire genome and assignment of potential protein-coding regions. DNA Res. 3: 109–136.

Keller, Y., Bouvier, F., d'Harlingue, A. & Camara, B. (1998). Metabolic compartmentation of plastid prenyllipid biosynthesis: Evidence for the involvement of a multifunctional geranylgeranyl reductase. Eur J Biochem. 251 413–7.

Lopez, J. C., Ryan, S. & Blankenship, R. E. (1996). Sequence of the bchG gene from Chloroflexus aurantiacus: relationship between chlorophyll synthase and other polyprenyltransferases. J. Bacteriol. 178: 3369–3373.

Norris, S. R., Shen, X. & DellaPenna, D. (1998). Complementation of the Arabidopsis pds1 mutation with the gene encoding p-hydroxyphenylpyruvate dioxygenase. Plant Phys. 117:1317–1323.

Pennock, J. F. (1985). Biosynthesis of plastoquinone. Meth. Enzymol. 110:313–319.

Seffens, W., Almoguera, C., Wilde, H., Vonder Haar, R. & Thomas, T. (1990). Molecular analysis of a phylogenetically conserved carrot gene: developmental and environmental regulation. Dev. Genet. 11:65–76.

Soll, J. (1987). α-Tocopherol and plastoquinone synthesis in chloroplast membranes. Meth. Enzymol. 148:383–392.

Soll, J., Kemmerling, M. & Schultz, G. (1980). Tocopherol and plastoquinone synthesis in Spinach chloroplast subfractions. Arch. Biochem. Biophys. 204:544–550.

Williams, J. G. K. (1988). Construction of specific mutations in Photosystem II photosynthetic reaction center by genetic engineering methods in Synechocystis 6803. Meth. Enzymol. 167:766–778.

The present invention will be further described by reference to the following detailed examples. It is understood, however, that there are many extensions, variations, and modification on the basic theme of the present invention beyond that shown in the examples and description, which are within the spirit and scope of the present invention. All publications, patents, and patent application cited herein are hereby incorporated by reference.

What is claimed is:

1. A method for increasing the level of tocopherol in a plant, comprising:
   (a) stably transforming a plant cell with a polynucleotide operably linked to a promoter, wherein the polynucleotide is selected from the group consisting of;
      i) a polynucleotide comprising the sequence set forth in SEQ ID NO: 3, and
      ii) a polynucleotlde that encodes the polypeptide of SEQ ID NO: 4,
   (b) growing the plant cell under plant growing conditions to produce a regenerated plant which expresses the polynucleotide for a time sufficient to increase the level of tocopherol in the plant.

2. The method of claim 1, wherein the polynudeotide comprises the sequence set forth in SEQ ID NO: 3.

3. The method of claim 1, wherein the plant is corn, soybean, sunflower, sorghum, canola, wheat, alfalfa, cotton, rice, barley, millet, *Arabidopsis thaliana*, tomato, Brassica, pepper, potato, apple, spinach, or lettuce.

* * * * *

UNITED STATES PATENT AND TRADEMARK OFFICE
CERTIFICATE OF CORRECTION

PATENT NO. : 6,787,683 B1
DATED : September 7, 2004
INVENTOR(S) : Dean Della Penna et al.

It is certified that error appears in the above-identified patent and that said Letters Patent is hereby corrected as shown below:

Title page,
Item [56], References Cited, OTHER PUBLICATIONS,
"Jiang" reference, should read as follows:
-- Jiang et al., Nature, vol. 366, Nov. 4, 1993, pp. 84-93." --
"Walbot, V." reference, should read as follows:
-- Walbot, V., 1999, GenBank Accession No. Al612332, Maize ESTs from various cDNA libraries sequenced at Stanford University. --
"Walbot, V.," reference, should read as follows:
-- Walbot, V., 1999, GenBank Accession No. Al948381, Maize ESTs from various cDNA libraries sequenced at Stanford University. --

Signed and Sealed this

Twenty-fifth Day of January, 2005

JON W. DUDAS
*Director of the United States Patent and Trademark Office*